(12) United States Patent
Ward et al.

(10) Patent No.: US 6,861,222 B2
(45) Date of Patent: Mar. 1, 2005

(54) NUCLEIC ACID DETECTION USING STRUCTURED PROBES

(75) Inventors: David C. Ward, Madison, CT (US); Patricia Bray-Ward, Madison, CT (US)

(73) Assignee: Yale University, New Haven, CT (US)

( * ) Notice: Subject to any disclaimer, the term of this patent is extended or adjusted under 35 U.S.C. 154(b) by 242 days.

(21) Appl. No.: 10/037,469

(22) Filed: Nov. 9, 2001

(65) Prior Publication Data

US 2003/0059786 A1 Mar. 27, 2003

Related U.S. Application Data

(60) Provisional application No. 60/247,407, filed on Nov. 9, 2000.

(51) Int. Cl.[7] .............................. C12Q 1/68; C12P 19/34; C07H 21/02
(52) U.S. Cl. ....................... 435/6; 435/91.2; 435/91.21; 536/23.1; 536/24.3
(58) Field of Search ....................... 435/6, 91.2, 91.21; 536/23.1, 24.3

(56) References Cited

U.S. PATENT DOCUMENTS

| | | | |
|---|---|---|---|
| 5,001,050 A | | 3/1991 | Blanco et al. |
| 5,198,543 A | | 3/1993 | Blanco et al. |
| 5,334,711 A | | 8/1994 | Sproat et al. |
| 5,429,807 A | | 7/1995 | Matson et al. |
| 5,599,695 A | | 2/1997 | Pease et al. |
| 5,654,413 A | | 8/1997 | Brenner |
| 5,854,033 A | | 12/1998 | Lizardi |
| 5,866,336 A | | 2/1999 | Nazarenko et al. |
| 5,871,928 A | | 2/1999 | Fedor et al. |
| 5,876,924 A | | 3/1999 | Zhang et al. |
| 5,925,517 A | * | 7/1999 | Tyagi et al. ............... 435/6 |
| 5,942,391 A | | 8/1999 | Zhang et al. |
| 6,033,881 A | | 3/2000 | Himmler et al. |
| 6,096,880 A | | 8/2000 | Kool et al. |
| 6,117,635 A | | 9/2000 | Nazarenko et al. |
| 6,143,495 A | | 11/2000 | Lizardi et al. |
| 6,183,960 B1 | | 2/2001 | Lizardi |
| 6,210,884 B1 | | 4/2001 | Lizardi |
| 6,221,603 B1 | | 4/2001 | Mahtani et al. |
| 6,255,082 B1 | | 7/2001 | Lizardi et al. |
| 6,277,607 B1 | * | 8/2001 | Tyagi et al. ............ 435/91.2 |
| 6,291,187 B1 | | 9/2001 | Kingsmore et al. |
| 6,316,229 B1 | * | 11/2001 | Lizardi et al. ........... 435/91.1 |
| 6,323,009 B1 | | 11/2001 | Lasken et al. |
| 6,329,150 B1 | | 12/2001 | Lizardi et al. |
| 6,344,329 B1 | | 2/2002 | Lizardi |

FOREIGN PATENT DOCUMENTS

| | | | |
|---|---|---|---|
| EP | 0 745 690 A2 | | 12/1996 |
| WO | WO 97/19193 | * | 5/1997 |
| WO | WO 99/31276 | | 6/1999 |
| WO | WO 00 71562 | | 11/2000 |

OTHER PUBLICATIONS

Benseler et al. Hammer–like Molecules Containing Non–Nucleoside Linkers Are Active RNA Catalysts. *J. Am. Chem. Soc.* 115:8483–8484.
Birkenmeyer et al. DNA probe amplification methods. *J. Virological Methods* 35:117–126 (1991).
Boehmer et al. Herpes Simplex Virus Type 1 ICP8: Helix–Destabilizing Properties. *J. Virology* 67(2):711–715 (1993).
Bonnet et al. Thermodynamic basis of the enhanced specificity of structured DNA. *Proc. Natl. Acad. Sci. USA* 96(11):6171–6 (1999).
Chatterjee et al. Cloning and overexpression of the gene encoding bacteriophage T5 DNA polymerase. *Gene* 97:13–19 (1991).
Cremer et al. Detection of chromosome aberrations in metaphase and interphase tumor cells by in situ hybridization using *chromosome–specific* library probes. *Hum. Genet.* 80(3):235–46 (1988).
Fire et al. Rolling replication of short DNA circles. *Proc. Natl. Acad. Sci. USA* 92:4641–4645 (1995).
Fu et al. Hammerhead Ribozymes Containing Non–Nucleoside Linkers Are Active RNA Catakysts. *J. Am. Chem. Soc.* 116:4591–4598 (1994).
Guo et al. Direct fluorescence analysis of genetic polymorphisms by hybridization with oligonucleotide arrays on glass supports. *Nucleic Acids Res.* 22:5456–5465 (1994).
Haaf et al. High resolution ordering of YAO contigs using extended chromatin and chromosomes. *Hum. Mol. Genet.* 3(4):629–33 (1994).
Hoy et al. Bromodeoxyuridine/DNA analysis of replication in CHO cells after exposure to UV light. *Mutation Research* 290:217–230 (1993).
Itakura et al. Synthesis and Use of Synthetic Oligonucleotides. *Ann. Rev. Biochem.* 53:323–356 (1984).

(List continued on next page.)

*Primary Examiner*—Jeffrey Fredman
(74) *Attorney, Agent, or Firm*—Needle & Rosenberg, P.C.

(57) ABSTRACT

Disclosed are compositions and a method for detection of nucleic acid sequences. The disclosed method uses a structured probe to distinguish between sequences. Structured probes are bifunctional molecules where one function is as a probe to a target nucleic acid sequence and the other function is as a detection sequence to facilitate detection of the probe. Structured probes include a detection sequence, sequence complementary to a target sequence, and sequences that form duplex regions (higher order structures). The duplex region is stable unless the probe hybridizes to the target sequence. The disclosed method involves hybridizing the structured probe to a target sequence and detecting the detection sequence on the structured probe. The detection sequence is available for detection only if the duplex region of the structured probe is disrupted. This links detection of the structured probe with the hybridization of the structured probe to the target sequence.

56 Claims, 6 Drawing Sheets

OTHER PUBLICATIONS

Jacobsen et al. The N-Terminal Amino-Acid Sequences of DNA Polymerase I from *Eschericha coli* and of the Large and the Small Fragments Obtained by a Limited Proteolysis. *Eur. J. Biochem.* 45:623–627 (1974).

Jung et al. Bacteriphage PRD1 DNA polymerases. *Proc. Natl. Acad. Sci. USA* 84:8287–8291 (1987).

Kaboord et al. Accessory proteins function as matchmakers in the assembly of the T4 DNA polymerase holoenzyme. *Curr. Biol*, 5:149–157 (1995).

Kerkhof. A Comparison of Substrates for Quantifying the Signal from a Nonradiolabeled DNA Probe. *Anal. Biochem.* 205:359–364 (1992).

Khrapko et al. Hybridization of DNA With Oligonucleotides Immobilized in Gel: A convenient Method For Detecting Single Base Substitutions. *Mol. Biol. (Mosk)(USSR)* 25:718–730 (1991).

Kong et al. Characterization of a DNA Polymerase from the Hyperthermophile Archaea *Thermococcus litoralis. J. Biol. Chem.* 268:1965–1975 (1993).

Landegren. Molecular mechanics of nucleic acid sequence amplification. *Trends Genetics* 9:199–202 (1993).

Langer et al. Enzymatic synthesis of biotin–labeled polynucleotides: Novel nucleic acid affinity probes. *Proc. Natl. Acad. Sci USA* 78:6633 (1981).

Lesnick et al. Relative Thermodynamic of DNA, RNA, and DNA–RNA Hybrid Duplexes: Relationship with Base Composition and Structure. *Biochemistry* 34:10807–10815 (1995).

Letsinger et al. Use of a Stilbenedicarboxamide Bridge in Stabilizing, Monitoring, and Photochemically Altering Folded Conformations of Oligonucleotides. *J. Am. Chem. Soc.* 117:7323–7328 (1995).

Lipshutz et al. Using Oligonucleotide Probe Arrays To Access Genetic Diversity. *BioTechniques* 19:442–447 (1995).

Lizardi et al. Mutation detection and single–molecule counting using isothermal rolling–circle amplification. *Nature Genet.* 19:225–232 (1998).

Lyamichev et al. Polymorphism identification and quantitative detection of genomic DNA by invasive cleavage of oligonucleotide probes. *Nat. Biotech.* 17:292–296 (1999).

Matsumoto et al. Primary structure of bacteriophage M2 DNA polymerase: Conserved segments within protein–priming DNA polymerases and DNA polymerase I of *Escherichia coli. Gene* 84:247 (1989).

McGraw et al. Sequence–Dependent Oligonucleotide–Target Duplex Stabilities: Rules form Empirical Studies with a Set of Twenty–Mers. *Biotechniques* 8:674–678 (1990).

Moretti et al. Enhancement of PCR Amplification Yield and Specific Using AmplITaq Gold™ DNA Polymerase. *Biotechniques* 25:716–722 (1998).

Narang et al. Chemical Synthesis of Deoxyoligonucleotides by the Modified Treister Method. *Methods Enzymol.* 65:610–620 (1980).

Nielson et al. Peptide Nucleic Acid (PNA). A DNA Mimic with a Peptide Backbone. *Bioconjug. Chem.* 5:3–7 (1994).

Parra et al. High resolution visual mapping of stretched DNA by fluorescent hybridization. *Nature Genet.* 5:17–21 (1993).

Pease et al. Light–generated oligonucleotide arrays for rapid DNA sequence analysis. *Proc. Natl. Acad. Sci. USA* 91(11):5022–5026 (1994).

Picoult–Newberg et al. Mining SNPs From EST Databases. *Genome Res.* 9(2):167–74 (1999).

Rigler et al. Differences in the Mechanism of Stimulation of T7 DNA Polymerase by Two Binding Modes of *Escherichia coli* Single–stranded DNA–binding Protein. *J. Biol. Chem.* 270:8910–8919 (1995).

Ross et al. High level multiplex genotyping by MALDI–TOF mass spectrometry. *Nat. Biotechnol.* 16(13):1347–51 (1998).

Ryan et al. Non–PCR–Dependent Detection of the Factor V Leiden Mutation From Genomic DNA using a Homogeneous Invader Microtiter Plate Assay. *Mol. Diagn.* 4:135–144 (1999).

Rychlik et al. Optimization of the annealing temperature for DNA amplification in vitro. *Nucleic Acids Res.* 18:6409–6412 (1990).

Sambrook et al. *Molecular Cloning: A Laboratory Manual*, $2^{nd}$ Edition (Cold Spring Harbor Laboratory Press, Cold Spring Harbor, NY) Chapters 5, 6 (1989).

Schena et al. Quantitative Monitoring of Gene Expression Patterns with s Complementary DNA Microarray. *Science* 270:467–470 (1995).

Shi et al. Technologies for Detecting Genetic Polymorphisms in Pharmacogenomics. *Mol. Diagn.* 4(4):343–51 (1999).

Siegel et al. A Novel DNA Helicase from Calf Thymus. *J. Biol. Chem.* 267:13629–13635 (1992).

Skaliter et al. Rolling circle DNA replication in vitro by a complex of herpes simplex virus type 1–encoded. *Proc. Natl. Acad. Sci. USA* 91(22):10665–10669 (1994).

Stimpson et al. Real–time detection of DNA Hybridization and melting on oligonucleotide arrays by optical wave guides. *Proc. Natl. Acad. Sci. USA* 92:6379–6383 (1995).

Tabor et al. Selective Inactivation of the Exonuclease Activity of Bacteriophage T7 DNA Polymerase by in Vitro Mutagenesis. *J. Biol. Chem.* 264:6447–6458 (1989).

Tabor et al. Selective Oxidation of the Exonuclease Domain of Bacteriophage T7 DNA Polymerase. *J. Biol. Chem.* 262:15330–15333 (1987).

Tang et al. Chip–based Genotyping by mass spectrometry. *Proc. Natl. Acad. Sci. USA* 96(18):10016–20 (1999).

Tsurumi et al. Functional Interaction between Epstein–Barr Virus DNA Polymerase Catalytic Subunit and Its Accessory Subunit In Vitro. *J. Virology* 67(12):7648–7653 (1993).

Tyagi et al. Molecular Beacons: Probes that Flouresce upon Hybridization. *Nat. Biotech.* 14(3):303–308 (1996).

Vet et al. Multiplex detection of four pathogenic retroviruses using molecular beacons. *Proc. Natl. Acad. Sci. USA* 96(11):6394–9 (1999).

Vogelstein et al. Supercoiled Loops and Eucaryotic DNA Replication. *Cell* 22(1.1):79–85 (1980).

Wang et al. Large–Scale Identification, Mapping, and Genotyping of Single–Nucleotide Polymorphisms in the Human Genome. *Science* 280(5366):1077–82 (1998).

Wansick et al. Flourescent Labeling of Nascent RNA Reveals Transcription by RNA Polymerase II in Domains Scattered Throughout the Nucleus. *J. Cell Biology* 122:283–293 (1993).

Wiegant et al. High–resolution in situ hybridization using DNA halo preparations. *Hum. Mol. Genet.* 1(8):587–91 (1992).

Yu et al. Cyanine dye dUTP analogs foe enzymatic labeling for DNA probes *Nucleic Acids Res.* 22:3226–3232 (1994).

Yunis et al. The Characterization of High–Resolution G–Banded Chromosomes of Man. *Chromosoma* 67(4):293–307 (1978).

Zhu et al. Purification and characterization of PRD1 DNA polymerase. *Biochim. Biophys. Acta.* 1219:267–276 (1994).

Zijderveld et al. Helix–Destabilizing Properties of the Adenovirus DNA–Binding Protein. *J. Virol.* 68(2):1158–1164 (1994).

Baner et al. "Signal Amplification of Padlock Probes by Rolling Circle Replication" *Nucleic Acids Research* 26(22):5073–5078 (1998), XP–002112357.

Nuovo, et al. "In Situ Amplification Using Universal Energy Transfer–labeled Primers" *Journal of Histochemical Society* 47(3):273–279 (1999), XP008002684.

Gusev et al. Rolling Circle Amplification: A New Approach to Increase Sensitivity for Immunohistochemistry and Flow Cytometry, *American Journal of Pathology*, 159(1):63–69 (Jul. 2001).

Mullenix et al. Allergen–specific IgE Detection on Microarrays Using Rolling Circle Amplification; Correlation with in Vitro Assays for Serum IgE, *Clinical Chemistry*, 47(10):1926–1929 (2001).

Schweitzer et al. Immunoassays with Rolling Circle DNA Amplification: A Versatile Platform for Ultrasensitive Antigen Detection, *PNAS*, 97(18):10113–10119 (Aug. 29, 2000).

Schweitzer et al. Multiplexed Protein Profiling on Microarrays by Rolling–Circle Amplification, *Nature Biotechnology*, 20:359–365 (Apr. 2002).

* cited by examiner

A

B

C

D

E

F

G

H

NUCLEIC ACID DETECTION USING STRUCTURED PROBES

CROSS-REFERENCE TO RELATED APPLICATIONS

This application claims benefit of U.S. Provisional Application No. 60/247,407, filed Nov. 9, 2000. Application Ser. No. 60/247,407, filed Nov. 9, 2000, is hereby incorporated herein by reference in its entirety.

STATEMENT REGARDING FEDERALLY SPONSORED RESEARCH

This invention was made with government support under Grants NIH-GM057652 and NIH HG000272 awarded by the NIH. The government has certain rights in the invention.

FIELD OF THE INVENTION

The disclosed invention is in the general field of nucleic acid detection, and specifically in the field of detection of nucleic acids through target-specific signal amplification.

It is an object of the present invention to provide a method and compositions for detecting nucleic acid sequence with a combination of specificity and sensitivity.

It is another object of the disclosed invention to detect nucleic acid sequences while discriminating between closely related sequences.

It is another object of the present invention to provide a method and compositions for detecting the amount and location of nucleic acid sequences with a combination of specificity and sensitivity.

BACKGROUND OF THE INVENTION

Efficient analysis of genes and gene expression will require sensitive, quantitative, high-throughput procedures that can simultaneously analyze many alleles with relatively low cost. A number of methods have been developed which permit the implementation of extremely sensitive diagnostic assays based on nucleic acid detection. Most of these methods employ exponential amplification of targets or probes. These include the polymerase chain reaction (PCR), ligase chain reaction (LCR), self-sustained sequence replication (3SR), nucleic acid sequence based amplification (NASBA), strand displacement amplification (SDA), and amplification with Qβ replicase (Birkenmeyer and Mushahwar, *J. Virological Methods,* 35:117–126 (1991); Landegren, *Trends Genetics,* 9:199–202 (1993)).

While all of these methods offer good sensitivity, with a practical limit of detection of about 100 target molecules, all of them suffer from relatively low precision in quantitative measurements. This lack of precision manifests itself most dramatically when the diagnostic assay is implemented in multiplex format, that is, in a format designed for the simultaneous detection of several different target sequences.

Fluorescence in situ hybridization is a useful method of determining the physical position of sequences relative to each other in the genome. However, the ability to detect sequences decreases as the size of the target sequence decreases so that detection of targets that are less than 500 bases in length is very difficult or impossible.

A number of different techniques have been developed specifically for the detection of single nucleotide polymorphisms (SNPs) or point mutations (PMs) in nucleic acids. These include solution-based assays using molecular beacon probes (Vet et al., Proc Natl Acad Sci USA 96(11):6394–9 (1999)); selective nuclease cleavage (Lyamichev et al., Nature Biotechnology 17, 292–296 (1999); Ryan et al., Mol. Diagn. 4:135–144 (1999)); direct DNA or cDNA sequence analysis (Wang et al., Science 280(5366):1077–82 (1998)); mass differential of allele discriminating oligonucleotides separated by time-of-flight mass spectrometry (Ross et al., Nat Biotechnol 16(13):1347–51 (1998); Tang et al., Proc Natl Acad Sci USA 96(18):10016–20 (1999)); differential electrophoretic mobility of DNA restriction fragments with zero or one mismatched base pair (Shi et al., Mol Diagn 4(4):343–51 (1999)); hybridization to oligonucleotide microarrays with allele discrimination being achieved by differential hybridization (Lipshutz et al., Bio Techniques. 19:442–447 (1995); Wang et al., Science 280(5366):1077–82 (1998)); selective DNA ligation (Shi et al., Mol Diagn 4(4):343–51 (1999)); and single nucleotide extension of the tethered oligonucleotide using mixture of four dideoxynucleotide triphosphates, each labeled with a distinct fluorophore (Picoult-Newberg et al., Genome Res 9(2):167–74 (1999)).

Each of these methods suffers from one or more drawbacks. First, both solution and electrophoretic mobility assays require prior synthesis of selected PCR amplicons or very large amounts of genomic DNA. They are also less amenable to high throughput formats. Direct sequence analysis of multiple loci in extensive pedigrees is both expensive and best conducted in dedicated sequencing laboratories. Mass spectrometry and oligonucleotide arrays offer considerable promise as high throughput SNP or PM analytical systems, but they too have technical limitations. The current detection sensitivities of array readers and Maldi-TOF spectrometers necessitate that each locus be amplified by PCR prior to analysis. Although oligonucleotide arrays can be constructed with 10×5 or more individual oligonucleotides per array, multiplexing PCR reactions beyond 100–200 primer pairs is extremely difficult and time consuming, thus the full analytical potential of large arrays is difficult to achieve. The current level of multiplexing of oligonucleotide mass tags is also in the 100–200 range. In the absence of better DNA amplification technology and/or a significant increase in detection sensitivity, both mass spectrometry and array analysis of SNPs and PMs will be sample size driven and dependent on prior DNA amplification.

Rolling Circle Amplification (RCA) driven by DNA polymerase can replicate circular oligonucleotide probes with either linear or geometric kinetics under isothermal conditions (Lizardi et al., *Nature Genet.* 19: 225–232 (1998); U.S. Pat. No. 5,854,033 to Lizardi; PCT Application No. WO 97/19193). If a single primer is used, RCA generates in a few minutes a linear chain of hundreds or thousands of tandemly-linked DNA copies of a target that is covalently linked to that target. Generation of a linear amplification product permits both spatial resolution and accurate quantitation of a target. DNA generated by RCA can be labeled with fluorescent oligonucleotide tags that hybridize at multiple sites in the tandem DNA sequences. RCA can be used with fluorophore combinations designed for multiparametric color coding (PCT Application No. WO 97/19193), thereby markedly increasing the number of targets that can be analyzed simultaneously. RCA technologies can be used in solution, in situ and in microarrays. In solid phase formats, detection and quantitation can be achieved at the level of single molecules (Lizardi et al., 1998).

Ligation-mediated Rolling Circle Amplification (LM-RCA) involves circularization of a probe molecule hybridized to a target sequence and subsequent rolling circle amplification of the circular probe (U.S. Pat. No. 5,854,033 to Lizardi; PCT Application No. WO 97/19193). During amplification, the probe can become separated from the target sequence as it rolls. This can diminish the quality of spatial information obtained about the target.

BRIEF SUMMARY OF THE INVENTION

Disclosed are compositions and a method for detection of nucleic acid sequences. The disclosed compositions allow sensitive discrimination between closely related nucleic acid sequences. The disclosed method to distinguish between sequences uses probes that adopt a higher order structure through intramolecular duplex formation. The probes are referred to herein as structured probes. Structured probes are bifunctional molecules where one function is as a probe to a target nucleic acid sequence and the other function is as a detection sequence to facilitate detection of the probe. Structured probes include a detection sequence, sequence complementary to a target sequence, and sequences that form duplex regions (higher order structures). The duplex region is stable unless the probe hybridizes to the target sequence. The disclosed method involves hybridizing the structured probe to a target sequence and detecting the detection sequence on the structured probe. The detection sequence can be detected directly or can mediate signal amplification (with the amplified signal being detected). The detection sequence is available for detection only if the duplex region of the structured probe is disrupted. This links detection of the detection sequence with the hybridization of the structured probe to the target sequence. Preferred forms of structured probes have duplex regions that remain stable unless the probe is hybridized to a perfectly matched target sequence.

Preferred structured probes include a specialized form of rolling circle replication primer as the detection sequence. Hybridization of the structured probe to the target sequence can then be detected by replicating an amplification target circle (ATC) using the rolling circle replication primer on the structured probe. Rolling circle replication of the ATC produces many tandemly repeated complements of the ATC. The rolling circle replication primer is available to prime replication only if the duplex region of the structured probe is disrupted. This links the replication of the ATC with the hybridization of the structured probe to the target sequence.

The disclosed method is useful for detecting any desired sequence. In particular, the disclosed method can be used to localize or amplify signal from any desired sequence. For example, the disclosed method can be used to probe transgenic cells, bacterial or yeast colonies, cellular material (for example, whole cells, DNA fibers, interphase nuclei, or metaphase chromosomes on slides, arrayed genomic DNA, RNA). The disclosed method is particularly useful for detecting sequence variants of a target sequence. For example, insertions, deletions, repeats, and single nucleotide polymorphisms (SNPs), can be detected. Specificity of such detection is aided by sensitivity of the duplex region to mismatches.

The disclosed method is applicable to numerous areas including, but not limited to, disease detection, mutation detection, RNA expression profiling, gene discovery, gene mapping (molecular haplotyping), agricultural research, and virus detection. Preferred uses include SNP detection in situ in cells, on microarrays, on DNA fibers, and on genomic DNA arrays; detection of RNA in cells; RNA expression profiling; molecular haplotyping; mutation detection; detection of abnormal RNA (for example, overexpression of an oncogene or absence of expression of a tumor suppressor gene); expression in cancer cells; detection of viral genome in cells; viral RNA expression; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

BRIEF DESCRIPTION OF THE DRAWINGS

FIG. 3A is a diagram of an example of a hairpin structured probe forming a hairpin stem and loop structure. FIG. 3B is a diagram of an example of a curl structured probe forming a curl stem and loop structure. Region 1 is the second complementary portion and region 2 is the first complementary portion. Region 3 is the target probe portion. Junction 4 is the 5' to 5' junction of the two parts of the curl structured probe.

FIGS. 4A–4D are examples of structured probes forming a hairpin stem and loop structure. FIGS. 4E–4H are examples of structured probes forming a curl stem and loop structure. Note that either or both the first end and the second end can extend beyond the stem structure. The detection portion preferably extends to the second end of the probe. If the detection portion is a rolling circle replication primer it should extend to the second end of the probe (a 3' end). In the various structured probe structures shown, the rolling circle replication primer portion can overlap completely, overlap partially, or not overlap at all with the second complementary portion.

DETAILED DESCRIPTION OF THE INVENTION

Figure 1:
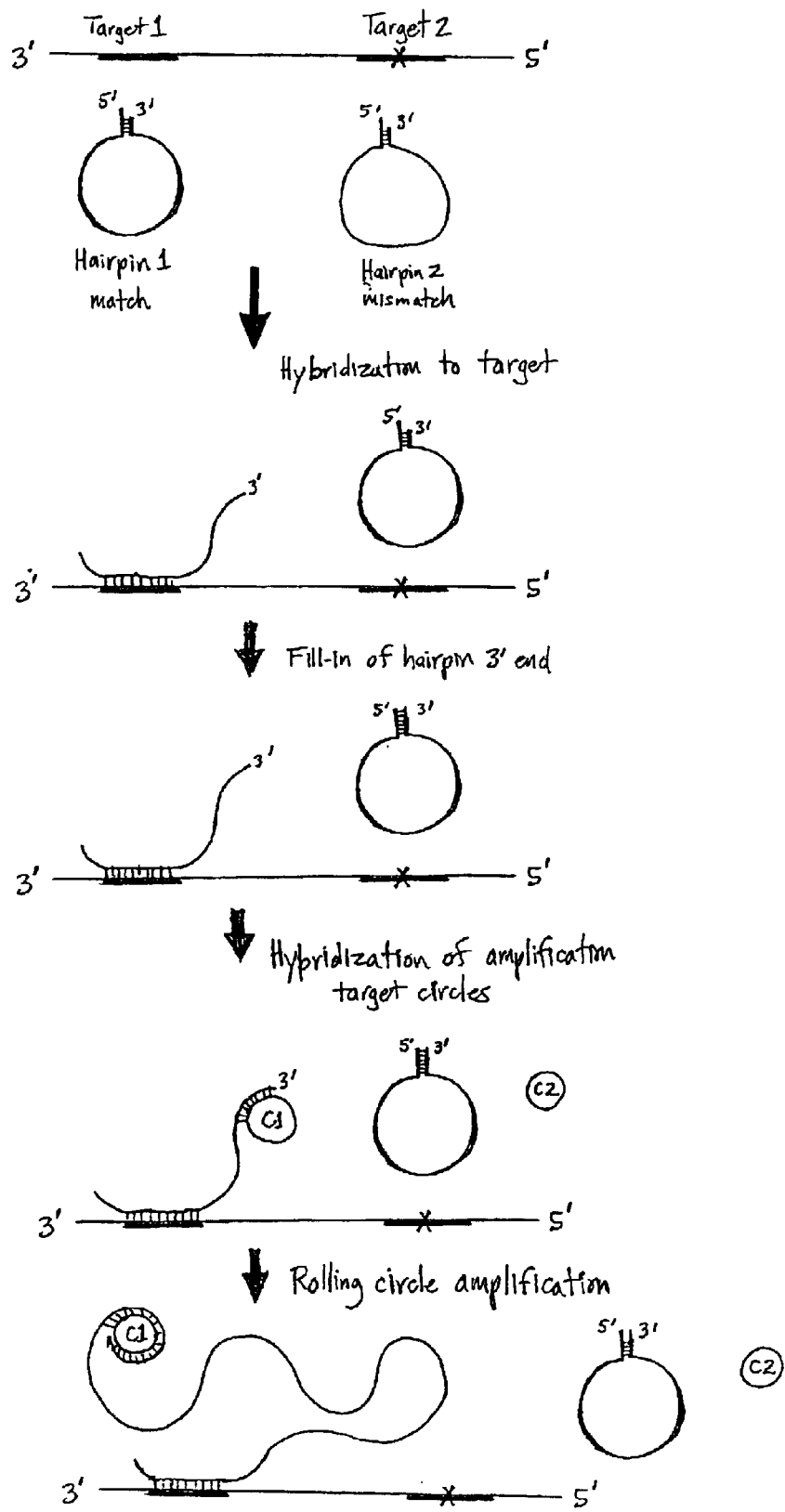
FIG. 1 is a diagram of an example of the disclosed method involving 3' extension to inactivate the structured probe.

The disclosed method and compositions are based on probe designs that have a higher efficiency of detection than previous rolling circle amplification probes. The disclosed structured probes are bifunctional molecules having a probe function and a detection function. These functions are embodied by including in the structured probes sequences complementary to a target sequence and sequences to facilitate detection of the hybridized probe. The structured probes are characterized by an allele discrimination capability that is markedly better that the comparable linear probes due to the competition between the structural interferences between folding due to intramolecular duplex formation and linear rigidity due to hybridization of the probe sequence to the target (Tyagi and Kramer, Nat Biotechnol 14(3):303–8 (1996); Bonnet et al., Proc Natl Acad Sci USA 96(11):6171–6 (1999)). Preferred structured probes will not hybridize to mismatched sequences under suitable conditions because duplex hybridization of probe to target does not effectively compete with intramolecular duplex formation of the structured probe. This makes the detection sequences on the probe unavailable for generation of a signal or unable to generate a signal. The presence of target causes the correctly matched structured probe to unfold, rendering the detection sequences available for signal generation.

The disclosed method involves mixing one or more different structured probes with one or more target samples and incubating under conditions that promote hybridization between the probes and target sequences in the samples. The duplex region of the structured probes is disrupted in a target-dependent manner (that is, by hybridization of the probes to the target sequences). The resulting signal event can be produced in any manner and by any mechanism the relies on the availability of the detection sequences. In preferred forms of the method, unique identification of multiple nucleic acid sequences in a single assay can be accomplished by associating unique detection sequences (part of the structured probe) with each the various nucleic acid sequences to be detected.

In a preferred form of the method, the detection sequences are a rolling circle replication primer. The probes are mixed with one or more amplification target circles (ATCs) and incubated under conditions that promote hybridization between the ATCs and the rolling circle replication primer portions of the probes. To amplify the signal, DNA polymerase is mixed with the probes and ATCs and incubated under conditions that promote replication of the ATCs. Replication of the ATC results in the formation of a long DNA strand containing numerous tandem repeats of the ATC sequence (the DNA is referred to as tandem sequence DNA). Unique identification of multiple nucleic acid sequences in a single assay is accomplished by associating unique rolling circle replication primer sequences (part of the structured probe) with each the various nucleic acid sequences to be detected. Each rolling circle replication primer sequence hybridizes to, and primes replication of, a unique ATC. Detection of the unique sequences of the various resulting tandem sequence DNAs (each derived from a different, nucleic acid sequence-specific ATC) indicates the presence in the nucleic acid sample of the target sequence identified by their cognate tandem DNA sequence.

The disclosed method is useful for detection, quantitation, and/or location of any desired nucleic acid sequences. The disclosed method can be multiplexed to detect numerous different nucleic acid sequences simultaneously or used in a single assay. Thus, the disclosed method is useful for detecting, assessing, quantitating, profiling, and/or cataloging RNA expression in nucleic acid samples. The disclosed method is also particularly useful for detecting and discriminating single nucleotide differences in nucleic acid sequences. This specificity is possible due to the sensitivity of the higher order structure in structured probes to mismatches between the target probe portion (in the structured probe) and a prospective target sequence. Thus, the disclosed is useful for detecting, assessing, quantitating, and/or cataloging single nucleotide polymorphisms, and other sequence differences between nucleic acids, nucleic acid samples, and sources of nucleic acid samples. In particular, the ratio of different polymorphs of a nucleic acid sequence in sample can be assessed due to the ability of the disclosed method to detect single copies of target sequences.

The disclosed method is applicable to numerous areas including, but not limited to, disease detection, mutation detection, RNA expression profiling, gene discovery, gene mapping (molecular haplotyping), agricultural research, and virus detection. Preferred uses include SNP detection in situ in cells, on microarrays, on DNA fibers, and on genomic DNA arrays; detection of RNA in cells; RNA expression profiling; molecular haplotyping, mutation detection, detection of abnormal RNA (for example, overexpression of an oncogene or absence of expression of a tumor suppressor gene), expression in cancer cells, detection of viral genome in cells, viral RNA expression; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

The structured probe design is very efficient and several variations in the design of these probes have been implemented to optimize the specificity of the structured-primed signal amplification reactions. The features of the disclosed probe have been demonstrated using several cystic fibrosis mutations, p53 mutations, and DRD2 alleles. Use of the disclosed probes for allele discrimination of DNA in solution and in situ using cultured cell lines has also been demonstrated. The disclosed probes also can be used in an array format where either the probes or the target nucleic acids are immobilized.

Materials

A. Structured Probes

A structured probe is an oligomer, preferably a single-stranded nucleic acid, that can form a duplex hairpin stem and loop or a curl stem and loop structure. The stem structure in the hairpin stem and loop structure and the curl stem and loop structure are referred to herein as duplex regions (or intramolecular hybrids). Structured probes are bifunctional, functioning both as probes to target nucleic acid sequences and for detection. Structured probes are designed such that detection is not possible unless the probe hybridizes to the target nucleic acid sequence. Structured probes include one or more complementary portions, a target probe portion, and a detection portion. For example, structured probes can include a second complementary portion and, in order from the first end of the probe to the second end of the probe, a first complementary portion, a target probe portion, and a detection portion. Preferred structured probes include a second complementary portion and, in order from the first end of the probe to the second end of the probe, a first complementary portion, a target probe portion, and a rolling circle replication primer portion (as the detection portion). The complementary portions of a structured probe can form a duplex region. The target probe portion is complementary to a target nucleic acid sequence. The detection portion should be inaccessible or non-functional (for generating a signal) when the probe forms the duplex region. This can be accomplished by, for example, embedding all or a part of the detection portion in the duplex region.

When the detection portion is a rolling circle replication primer, the detection portion should be at the second end of the probe and should be complementary to a primer complement portion of an ATC. This allows the primer portion to prime rolling circle replication. For this purpose, the second end of the probe has a 3' end and the rolling circle replication primer portion is in a 3' to 5' orientation relative to the second end. The rolling circle replication primer portion is complementary to a primer complement portion of an ATC.

Figure 3:
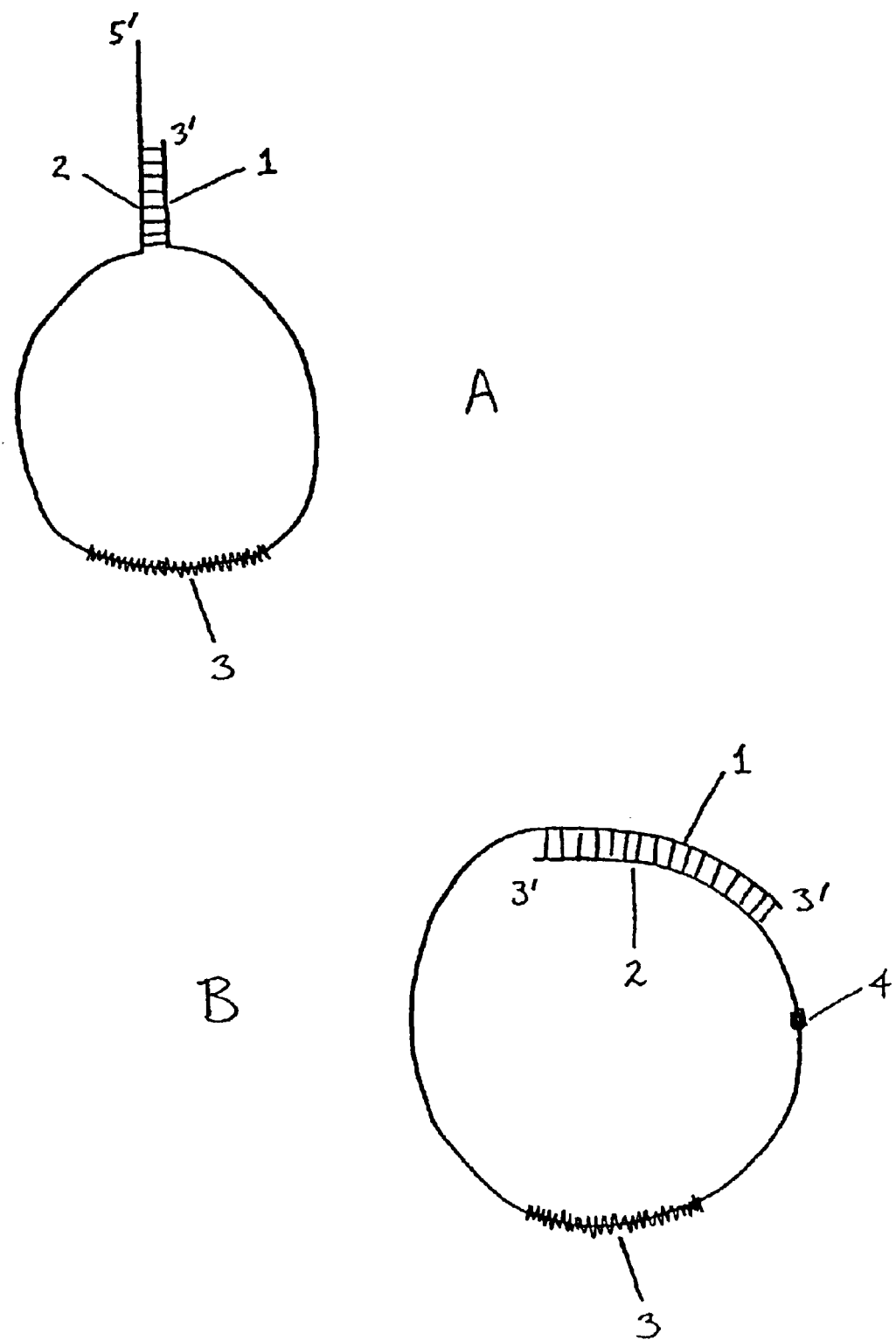
FIGS. 3A and 3B are diagrams of examples of structured probes.
Figure 4:
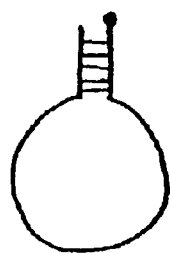
FIGS. 4A–4H are examples of different configurations of the disclosed structured probes. The terminal dots indicate 3' ends.
Figure 4:
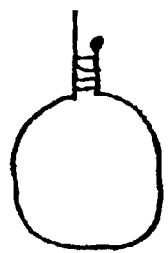
Figure 4:
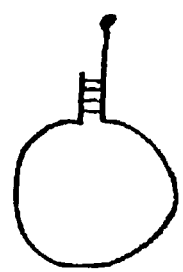
Figure 4:
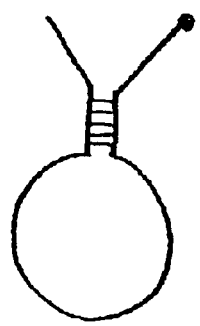
Figure 4:
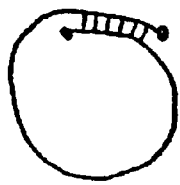
Figure 4:
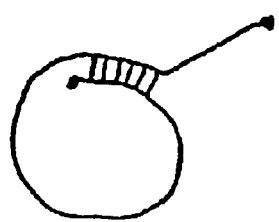
Figure 4:
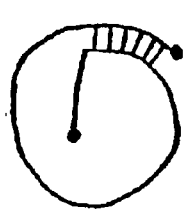
Figure 4:
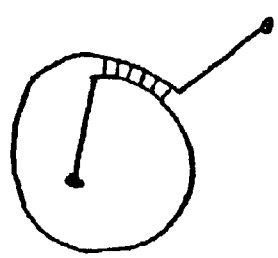

Structured probes form a hairpin stem and loop structure or a curl stem and loop structure, where the stem is formed by the complementary portions. Preferably, all or a part of the target probe portion is in the loop. An example of a structured probe forming a hairpin stem and loop structure is shown in FIG. 3A. Such a structured probe is referred to herein as a hairpin structured probe. An example of a structured probe forming a curl stem and loop structure is shown in FIG. 3B. Such a structured probe is referred to herein as a curl structured probe. The curl stem and loop structure is a result of a 5' to 5' junction in the structured probe that gives the curl structured probe two 3' ends. Hybridization of the target probe portion of a structured probe to the target nucleic acid sequence disrupts the duplex region (that is, the hairpin stem or curl stem). Preferred forms of structured probes are designed such that the probe undergoes a conformational change that disrupts its duplex region only if there is a correct match between the probe and target sequences. This allows the structured probe to be used in the disclosed method to distinguish related sequences.

For structured probes that form a hairpin stem and loop structure, it is preferred that the first end of the structured probe be a 5' end and the second end of the structured probe be a 3' end. In this case, it is preferred that the complementary portions, the target probe portion, and the detection portion are each in a 5' to 3' orientation relative to the first end. This is the simplest form of structured probe and can be a single oligonucleotide strand with all the nucleotides of the same polarity.

For structured probes that form a curl stem and loop structure, it is preferred that both the first end of the structured probe and the second end of the structured probe are 3' ends. At a minimum, the two complementary portions must have opposite polarities for the curl structure to form. This can be accomplished with a 5' to 5' junction between (a) a first complementary portion and the target probe portion and (b) the detection portion and a second complementary portion. Alternatively, a 5' to 5' junction can be placed between (a) the first complementary portion and (b) the target probe portion, the detection portion, and a second complementary portion. In the first case, it is preferred that the first complementary portion and target probe portion each be in a 3' to 5' orientation relative to the first end, and that the detection portion and second complementary portion each be in a 3' to 5' orientation relative to the second end. In the second case, it is preferred that the second complementary portion, detection portion, and target probe portion each be in a 3' to 5' orientation relative to the second end, and the first complementary portion be in a 3' to 5' orientation relative to the first end. It is preferred that the various portions of the probe each be 4 or more bases from the 5' to 5' junction.

Structured probes can have a variety of structures, some of which are suitable for particular forms of the disclosed method. For example, hairpin structured probes can be designed so that the detection portion either overlaps, partially or completely, or does not overlap, a complementary portion. Structured probes also can be designed so that a complementary portion either overlaps, partially or completely, or does not overlap, the detection portion. Where the detection portion and complementary portion overlap, the overlap can be partial—where only a portion of the detection portion overlaps the second complementary portion—or complete—where the detection portion and the second complementary portion are the same portion of the probe.

Where the detection portion overlaps part of a complementary portion, a portion of the detection portion can extend beyond the complementary portion toward the first end and into the loop. In this case, it is preferred that hybridization of a nucleic acid sequence to the portion of the detection portion extending beyond the complementary portion into the loop will not disrupt the duplex region. In some embodiments, a complementary portion can be at the second end of the probe. In this case, the complementary portion and the detection mechanism portion can completely overlap or a portion of the detection mechanism portion can extend beyond the complementary portion toward the first end and into the loop.

When the detection portion is a rolling circle replication primer, and when the rolling circle replication primer portion does not overlap the second complementary portion, the second complementary portion is placed closer to the first end of the probe than the rolling circle replication primer portion. Where the rolling circle replication primer portion partially overlaps the second complementary portion, a portion of the rolling circle replication primer portion can extend beyond the second complementary portion toward the first end and into the loop. In this case, it is preferred that hybridization of a nucleic acid sequence to the portion of the rolling circle replication primer extending beyond the second complementary portion into the loop will not disrupt the duplex region. Alternatively, a portion of the second complementary portion can extend beyond the rolling circle replication primer toward the first end. In some embodiments, the second complementary portion can be at the second end of the probe. In this case, the second complementary portion and the rolling circle replication primer portion can completely overlap, a portion of the rolling circle replication primer can extend beyond the second complementary portion toward the first end and into the loop, or a portion of the second complementary portion can extend beyond the rolling circle replication primer toward the first end.

Although not preferred, the complementary portions of structured probes need not be contiguous regions of the structured probe. That is, a given complementary portion can be made up of separated sequences in the structured probe that can form a hybrid with another, similarly interrupted complementary portion. In such a case there will be unpaired nucleotides in the duplex region formed by the complementary portions. Unless otherwise indicated, as used herein, the term "complementary portion" refers to portions of a structured probe that form duplex regions rather than to any complementary nucleic acid sequence in general.

The duplex region can include a nucleic acid cleavage site. Such a structured probe is useful for the forms of the disclosed method where cleavage is used to inactivate the structured probe. In this case, it is preferred that the rolling circle replication primer portion (if used as the detection portion) not overlap the second complementary portion. This prevents the cleaved structured probe from having any rolling circle replication primer sequences at the end of the probe following cleavage. The duplex region can include a recognition site for a ligand or protein that binds nucleic acid. Such a structured probe is useful for the forms of the disclosed method where binding is used to inactivate the structured probe.

The first complementary portion of a structured probe can be at the first end of the probe but need not be. Where the first complementary portion is not at the first end of the probe, the structured probe will have an unhybridized tail at the first end. Such a tail is useful for several purposes. For example, the tail can serve as a template for extension of the second end of the probe (which is hybridized to the first complementary portion). Such extension adds nucleotides to the second end of the probe which, in preferred forms of the probe, are not complementary to the ATC. In this way, extension of the second end can inactivate the structured probe.

The tail also can be used to associate the probe with a surface, substrate, or other solid support. Such immobilized probes can be used to associate target nucleic acids and/or signals generated by or from the probe with a particular substrate or location in an array. Although preferred, a tail is not required for immobilization of the structured probe.

Immobilized probes with a tail at the first end also can serve as a template for extension of the second end of the probe.

It is preferred that multiple structured probes are immobilized together, preferably in an array. In this case, it is preferred that the structured probes are located in a plurality of different predefined regions of the solid support. The distance between the different predefined regions of the solid support can be fixed or variable. Where multiple structured probes are used it is preferred that the structured probes collectively correspond to a plurality of target nucleic acid sequences.

Structured probes also can be associated with the solid support by hybridization of the probe to the target nucleic acid sequence, which itself is associated with the solid support. Examples of target nucleic acids associated with a solid support are arrays of nucleic acid samples, arrays of oligonucleotides (where the oligonucleotides are the target nucleic acids), fixed cells, fixed tissue samples, and tissue slices. In the case of an array of target nucleic acid sequences, the solid support can be made up of a plurality of target nucleic acid sequences located in a plurality of different predefined regions of the solid support.

A detection portion is a portion of a structured probe that can generate a signal or otherwise mediate detection of the probe. The detection portion can, for example, incorporate a signal generating component, serve as a tag for association (by hybridization, for example) of a label or signal generating component with the probe, or mediate amplification. A rolling circle replication primer (RCRP) portion is a detection portion of a structured probe having sequence complementary to the primer complement portion of an ATC. This sequence is referred to as the complementary portion of the RCRP portion. The complementary portion of a RCRP portion and the cognate primer complement portion can have any desired sequence so long as they are complementary to each other. In general, the sequence of the RCRP portion can be chosen such that it is not significantly complementary to any other portion of the ATC. The complementary portion of a rolling circle replication primer portion can be any length that supports specific and stable hybridization between the primer and the primer complement portion. Generally this is 10 to 35 nucleotides long, but is preferably 16 to 20 nucleotides long.

The target probe portion on a structured probe is preferably located in the loop region of the probe. This makes the target probe portion accessible for hybridization to its cognate target nucleic acid sequence. Part of the target probe portion also can be outside of the loop region. The target probe portion can be any length that supports specific and stable hybridization between the target probes and the target sequence. For this purpose, a length of 10 to 35 nucleotides for each target probe portion is preferred, with target probe portions 18 to 25 nucleotides long being most preferred. The design of the target probe portion should be coordinated with the length of the loop region and the length and hybrid strength of the complementary portions of the structured probe. In general, the target probe portion and the rest of the structured probe should be designed so that the duplex region is disrupted when the target probe portion hybridizes to its cognate target sequence but not when only mismatched sequence is available for hybridization. Principles of design of target probe portions and structured probe are analogous to those used for molecular beacon probes. Design of molecular beacon probes is described by Tyagi and Kramer, Nat Biotechnol 14(3):303–8 (1996), and Bonnet et al., Proc Natl Acad Sci USA 96(11):6171–6 (1999). The proximity-sensitive labels used in molecular beacon probes are not required in the disclosed structured probes.

Structured probes can have any composition that allows the target probe portion to hybridize to the corresponding target sequence, the complementary portions to hybridize, and the detection portion to mediate detection and/or signal amplification. Preferably, the detection portion, complementary portions, and target probe portion are oligonucleotides. The structured probe also can be, or include regions of, peptide nucleic acids and other oligonucleotide analogues. The structured probes also can include nucleoside and nucleotide analogues. In particular, the target probe portion, the complementary portions, and the detection portion can be chimeric; containing any combination of standard nucleotides, nucleotide analogues, nucleoside analogues, and oligonucleotide analogues.

The target probe portion, the complementary portions, and the detection portion of structured probes can be joined in any manner that allows the probe to function as described herein. In one form, the entire structured probe can be a single oligonucleotide or oligomer strand. Structured probes also can include linkers. In the context of a structured probe, a linker is any non-nucleotide chain, structure, or region that links two or more of the components of the structured probe together. For example, in one form, at least a portion of the loop of the probe is a linker. In particular, the junction between the detection portion and the target probe portion can be a linker structure. Many coupling chemistries are known and can be adapted for use in linking components of structured probes.

As used herein, oligomer refers to oligomeric molecules composed of subunits where the subunits can be of the same class (such as nucleotides) or a mixture of classes (such as nucleotides and ethylene glycol). It is preferred that the disclosed structured probes be oligomeric sequences, non-nucleotide linkers, or a combination of oligomeric sequences and non-nucleotide linkers. It is more preferred that the disclosed structured probes be oligomeric sequences. Oligomeric sequences are oligomeric molecules where each of the subunits includes a nucleobase (that is, the base portion of a nucleotide or nucleotide analogue) which can interact with other oligomeric sequences in a base-specific manner. The hybridization of nucleic acid strands is a preferred example of such base-specific interactions. Oligomeric sequences preferably are comprised of nucleotides, nucleotide analogues, or both, or are oligonucleotide analogues.

A non-nucleotide linker can be any molecule that can be covalently coupled to an oligomeric sequence. Preferred non-nucleotide linkers are oligomeric molecules formed of non-nucleotide subunits. Examples of such non-nucleotide linkers are described by Letsinger and Wu, (*J. Am. Chem. Soc.* 117:7323–7328 (1995)), Benseler et al., (*J. Am. Chem. Soc.* 115:8483–8484 (1993)) and Fu et al., (*J. Am. Chem. Soc.* 116:4591–4598 (1994)). Preferred non-nucleotide linkers, or subunits for non-nucleotide linkers, include substituted or unsubstituted $C_1$–$C_{18}$ straight chain or branched alkyl, substituted or unsubstituted $C_2$–$C_{18}$ straight chain or branched alkenyl, substituted or unsubstituted $C_2$–$C_{18}$ straight chain or branched alkynyl, substituted or unsubstituted $C_1$–$C_{18}$ straight chain or branched alkoxy, substituted or unsubstituted $C_2$–$C_{18}$ straight chain or branched alkenyloxy, and substituted or unsubstituted $C_2$–$C_{18}$ straight chain or branched alkynyloxy. The substituents for these preferred non-nucleotide linkers (or subunits) can be halogen, cyano, amino, carboxy, ester, ether, carboxamide, hydroxy, or mercapto.

As used herein, nucleoside refers to adenosine, guanosine, cytidine, uridine, 2'-deoxyadenosine, 2'-deoxyguanosine, 2'-deoxycytidine, or thymidine. A nucleoside analogue is a chemically modified form of nucleoside containing a chemical modification at any position on the base or sugar portion of the nucleoside. As used herein, nucleotide refers to a phosphate derivative of nucleosides as described above, and a nucleotide analogue is a phosphate derivative of nucleoside analogues as described above. The subunits of oligonucleotide analogues, such as peptide nucleic acids, are also considered to be nucleotide analogues.

As used herein, oligonucleotide analogues are polymers of nucleic acid-like material with nucleic acid-like properties, such as sequence dependent hybridization, that contain at one or more positions a modification away from a standard RNA or DNA nucleotide. A preferred example of an oligonucleotide analogue is peptide nucleic acid. The internucleosidic linkage between two nucleosides can be achieved by phosphodiester bonds or by modified phospho bonds such as by phosphorothioate groups or other bonds such as, for example, those described in U.S. Pat. No. 5,334,711.

B. Target Nucleic Acid Sequences

As used herein, a target nucleic acid sequence (or target sequence) is a nucleic acid sequence to which the disclosed target probe portions are associated. Any nucleic acid molecule can include a target sequence for use in the disclosed method. Preferred target sequences are in naturally occurring DNA molecules and RNA molecules such as mRNA, viral RNA, and ribosomal RNA.

The target samples containing target sequences can come from any source. For example, target sequences can be obtained from mRNA samples, nucleic acid libraries, cells, cultures, tissues, bodily fluids, urine, serum, biopsy samples, and environmental samples. Numerous other sources of nucleic acids are known or can be developed and any can be used with the disclosed method. Any nucleic acid sample can be used as a target sample in the disclosed method. Examples of suitable target samples include mRNA samples, nucleic acid libraries, whole cell samples, environmental samples, culture samples, tissue samples, bodily fluids, urine samples, serum samples, and biopsy samples. Numerous other sources of target samples are known or can be developed and any can be used with the disclosed method. A target sample is any solution or composition containing or potentially containing a target sequence. A target sample can take any form. A preferred form of target sample is a solid state target.

C. Amplification Target Circles

An amplification target circle (ATC) is a circular single-stranded DNA molecule, generally containing between 40 to 1000 nucleotides, preferably between about 50 to 150 nucleotides, and most preferably between about 50 to 100 nucleotides. Portions of ATCs have specific functions making the ATC useful for rolling circle amplification (RCA). These portions are referred to as the primer complement portion, the detection tag portions, the secondary target sequence portions, the address tag portions, and the promoter portion. The primer complement portion is a required element of an ATC. Detection tag portions, secondary target sequence portions, address tag portions, and promoter portions are optional. Generally, an ATC is a single-stranded, circular DNA molecule comprising a primer complement portion. Those segments of the ATC that do not correspond to a specific portion of the ATC can be arbitrarily chosen sequences. It is preferred that ATCs do not have any sequences that are self-complementary. It is considered that this condition is met if there are no complementary regions greater than six nucleotides long without a mismatch or gap. It is also preferred that ATCs do not have any sequences that are complementary to sequences in the structured probe other than the rolling circle replication primer portion. It is also preferred that ATCs containing a promoter portion do not have any sequences that resemble a transcription terminator, such as a run of eight or more thymidine nucleotides.

D. Tandem Sequence DNA

An ATC, when replicated, gives rise to a long DNA molecule containing multiple repeats of sequences complementary to the ATC. This long DNA molecule is referred to herein as tandem sequences DNA (TS-DNA). TS-DNA contains sequences complementary to the primer complement portion and, if present on the ATC, the detection tag portions, the secondary target sequence portions, the address tag portions, and the promoter portion. These sequences in the TS-DNA are referred to as primer sequences (which match the sequence of the rolling circle replication primer), spacer sequences (complementary to the spacer region), detection tags, secondary target sequences, address tags, and promoter sequences. If the tandem sequence DNA is itself replicated by strand displacement amplification, the resulting long DNA molecules containing multiple repeats of sequences matching the ATC are referred to as secondary tandem sequence DNA. If the secondary tandem sequence DNA is in turn replicated by strand displacement amplification, the resulting long DNA molecules containing multiple repeats of sequences complementary to the ATC are referred to as tertiary tandem sequence DNA. The curl structured probe can be designed so that the first end can function as a secondary strand displacement primer.

E. Arrays and Solid State Probes and Targets

The target sample, target nucleic acid sequences, and structured probes can be coupled to a substrate. Doing so is useful for a variety of purposes including immobilization of the reaction or reaction products, allowing easy washing of reagents and reactions during an assay, aiding identification or detection of structured probes, and making it easier to assay multiple samples simultaneously. In particular, immobilization of target sequences allows the location of the target sequences in a sample or array to be determined. For example, a cell or chromosome spread can be probed in the disclosed method to determine the presence and location of specific target sequences within a cell, genome, or chromosome.

Solid-state substrates to which target samples, target sequences, or structured probes can be attached can include any solid material to which nucleic acids can be attached, adhered, or coupled, either directly or indirectly. This includes materials such as acrylamide, cellulose, nitrocellulose, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. The solid support can be porous or nonporous. Solid-state substrates can have any useful form including thin films or membranes, beads, bottles, dishes, fibers, woven fibers, shaped polymers, particles and microparticles. Preferred forms for solid-state substrates are flat surfaces, especially those used for cell and chromosome spreads.

When structured probes are immobilized, it is preferred that the first ends of the probes are coupled to the solid support. Each of the immobilized target nucleic acid sequences or structured probes preferably is located in a different predefined region of the solid support. In this case, the distance between the different predefined regions of the solid support can be fixed or variable. When each of the structured probes is located in a different predefined region of the solid support, the location of tandem sequence DNA on the solid support indicates the presence in the target sample of the target nucleic acid sequence corresponding to the structured probe at that region of the solid support. The solid support can be made up of a plurality of structured probes located in a plurality of different predefined regions of the solid support. Preferably, the structured probes collectively correspond to a plurality of target nucleic acid sequences.

The solid support can be made up of at least one thin film, membrane, bottle, dish, fiber, woven fiber, shaped polymer, particle, bead, or microparticle, or at least two thin films, membranes, bottles, dishes, fibers, woven fibers, shaped polymers, particles, beads, microparticles, or a combination.

When target samples or sequences are immobilized, the location of tandem sequence DNA on the solid support indicates the presence in the target sample of the target nucleic acid sequence corresponding to that region of the solid support. The solid support can be made up of a plurality of target nucleic acid sequences located in a plurality of different predefined regions of the solid support. Preferably, the target nucleic acid sequences collectively correspond to a plurality of structured probes.

Methods for immobilization of nucleic acids to solid-state substrates are well established. In general, target samples and target sequences can be immobilized on a substrate as part of a nucleic acid sample or other sample containing target sequences. Target sequences and structured probes can be coupled to substrates using established coupling methods. For example, suitable attachment methods are described by Pease et al., *Proc. Natl. Acad. Sci. USA* 91(11):5022–5026 (1994), Guo et al., *Nucleic Acids Res.* 22:5456–5465 (1994), and Khrapko et al., *Mol Biol (Mosk) (USSR)* 25:718–730 (1991). A method for immobilization of 3'-amine oligonucleotides on casein-coated slides is described by Stimpson et al., *Proc. Natl. Acad. Sci. USA* 92:6379–6383 (1995).

Methods for producing arrays of nucleic acids on solid-state substrates are also known. Examples of such techniques are described in U.S. Pat. No. 5,871,928 to Fodor et al., U.S. Pat. No. 5,54,413, U.S. Pat. No. 5,429,807, and U.S. Pat. No. 5,599,695 to Pease et al. Microarrays of RNA targets can be fabricated, for example, using the method described by Schena et al., *Science* 270:487–470 (1995).

Although preferred, it is not required that a given array of target samples, target sequences, or structured probes be a single unit or structure. The set of sequences or probes may be distributed over any number of solid supports. For example, at one extreme, each target sequence, each target sample, or each structured probe may be immobilized in or on a separate surface, reaction tube, container, or bead.

A variety of cell and nucleic acid sample preparation techniques are known and can be used to prepare samples for use in the disclosed method. For example, metaphase chromosomes and interphase nuclei can be prepared as described by Cremer et al., *Hum Genet* 80(3):235–46 (1988), and Haaf and Ward, *Hum Mol Genet* 3(4):629–33 (1994), genomic DNA fibers can be prepared as described by Yunis et al., *Chromosoma* 67(4):293–307 (1978), and Parra and Windle, *Nature Genet.* 5:17–21 (1993), and Halo preparations can be prepared as described by Vogelstein et al., *Cell* 22(1 Pt 1):79–85 (1980), and Wiegant et al., *Hum Mol Genet.* 1(8):587–91 (1992).

F. Strand Displacement Primers

Primers used for strand displacement replication are referred to herein as strand displacement primers. One form of strand displacement primer, referred to herein as a secondary strand displacement primer, is an oligonucleotide having sequence matching part of the sequence of an ATC. This sequence is referred to as the matching portion of the strand displacement primer. This matching portion of a secondary strand displacement primer is complementary to sequences in tandem sequence DNA (TS-DNA). The matching portion of a secondary strand displacement primer may be complementary to any sequence in TS-DNA. However, it is preferred that it not be complementary to a TS-DNA sequence matching either the rolling circle replication primer portion of a structured probe or a tertiary strand displacement primer, if one is being used. This prevents hybridization of the primers to each other. The matching portion of a strand displacement primer can be any length that supports specific and stable hybridization between the primer and its complement. Generally this is 12 to 35 nucleotides long, but is preferably 18 to 25 nucleotides long.

It is preferred that secondary strand displacement primers also contain additional sequence at their 5' end that does not match any part of the first strand of the ATC. This sequence is referred to as the non-matching portion of the strand displacement primer. The non-matching portion of the strand displacement primer, if present, serves to facilitate strand displacement during DNA replication. The non-matching portion of a strand displacement primer may be any length, but is generally 1 to 100 nucleotides long, and preferably 4 to 8 nucleotides long.

Another form of strand displacement primer, referred to herein as a tertiary strand displacement primer, is an oligonucleotide having sequence complementary to part of the sequence of an ATC. This sequence is referred to as the complementary portion of the tertiary strand displacement primer. This complementary portion of the tertiary strand displacement primer matches sequences in TS-DNA. The complementary portion of a tertiary strand displacement primer may be complementary to any sequence in the first strand of the ATC. However, it is preferred that it not be complementary to a sequence matching the strand displacement primer. This prevents hybridization of the primers to each other. The complementary portion of a tertiary strand displacement primer can be any length that supports specific and stable hybridization between the primer and its complement. Generally this is 12 to 35 nucleotides long, but is preferably 18 to 25 nucleotides long. It is preferred that tertiary strand displacement primers also contain additional sequence at their 5' end that is not complementary to any part of the first strand of the ATC. This sequence is referred to as the non-complementary portion of the tertiary strand displacement primer. The non-complementary portion of the tertiary strand displacement primer, if present, serves to facilitate strand displacement during DNA replication. The non-complementary portion of a tertiary strand displacement primer may be any length, but is generally 1 to 100 nucleotides long, and preferably 4 to 8 nucleotides long.

Strand displacement primers may also include modified nucleotides to make them resistant to exonuclease digestion. For example, the primer can have three or four phosphorothioate linkages between nucleotides at the 5' end of the primer. Strand displacement primers can be used for strand displacement replication and strand displacement cascade amplification, both described in U.S. Pat. No. 5,854,033 and PCT Application No. WO 97/19193.

G. Address Probes

An address probe is an oligonucleotide having a sequence complementary to address tags on TS-DNA or transcripts of TS-DNA, or to detection portions of structured probes. The complementary portion of an address probe can be any length that supports specific and stable hybridization between the address probe and the address tag. For this purpose, a length of 10 to 35 nucleotides is preferred, with a complementary portion of an address probe 12 to 18 nucleotides long being most preferred. Address probes can contain a single complementary portion or multiple complementary portions. Preferably, address probes are coupled, either directly or via a spacer molecule, to a solid-state support. Such a combination of address probe and solid-state support are a form of solid-state detector. Address probes complementary to detection portions of structured probes can be used to directly detect structured probes without the need for rolling circle replication or other amplification (such as PCR). For this purpose, it is preferred that a multi-labeled or multi-tagged address probe be used.

Address probes also can contain numerous labels or detection tag sequences to increase the signal from any target sequence with which the address probe becomes associated. For example, an address probe can be branched to increase the density of labels or tag sequences. Address probe also can contain sequences that can be amplified using a nucleic acid amplification technique, including PCR and RCA.

H. Synthesis of Oligonucleotides

Structured probes, components of structured probes, strand displacement primers, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323–356 (1984), (phosphotriester and phosphite-triester methods), and Narang et al., *Methods Enzymol.* 65:610–620 (1980), (phosphotriester method). Protein nucleic acid molecules can be made using known methods such as those described by Nielsen et al., *Bioconjug. Chem.* 5:3–7 (1994).

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807–10815 (1995), McGraw et al., *Biotechniques* 8:674–678 (1990), and Rychlik et al., *Nucleic Acids Res.* 18:6409–6412 (1990).

I. Detection Probes

Detection probes are labeled oligonucleotides having sequence complementary to detection tags on TS-DNA, transcripts of TS-DNA, address probes, or detection portions of structured probes. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described below. Preferred labels are biotin and fluorescent molecules. A particularly preferred detection probe is a molecular beacon. Molecular beacons make use of fluorescent moieties where the fluorescent moieties fluoresce most strongly when the fluorescent moiety and a quencher moiety are not in proximity (Tyagi and Kramer, *Nature Biotechnology* 14:303–308 (1996)). The use of such probes eliminates the need for removal of unhybridized probes prior to label detection because the unhybridized detection probes will not produce a signal. This is especially useful in multiplex assays.

A preferred form of detection probe, referred to herein as a collapsing detection probe, contains two separate complementary portions. This allows each detection probe to hybridize to two detection tags in TS-DNA. In this way, the detection probe forms a bridge between different parts of the TS-DNA. The combined action of numerous collapsing detection probes hybridizing to TS-DNA will be to form a collapsed network of cross-linked TS-DNA. Collapsed TS-DNA occupies a much smaller volume than free, extended TS-DNA, and includes whatever detection label present on the detection probe. This result is a compact and discrete detectable signal for each TS-DNA. Collapsing TS-DNA is useful both for in situ hybridization applications and for multiplex detection because it allows detectable signals to be spatially separate even when closely packed. Collapsing TS-DNA is especially preferred for use with combinatorial multicolor coding.

TS-DNA collapse also can be accomplished through the use of ligand/ligand binding pairs (such as biotin and avidin) or hapten/antibody pairs. A nucleotide analog, BUDR, can be incorporated into TS-DNA during rolling circle replication. When biotinylated antibodies specific for BUDR and avidin are added, a cross-linked network of TS-DNA forms, bridged by avidin-biotin-antibody conjugates, and the TS-DNA collapses into a compact structure. Collapsing detection probes and biotin-mediated collapse also can be used together to collapse TS-DNA.

J. Detection Labels

To aid in detection and quantitation of amplified nucleic acids produced in association with structured probes, labels can be incorporated into, or coupled to, DNA probes. A label is any molecule that can be associated with DNA probes, directly or indirectly, and which results in a measurable, detectable signal, either directly or indirectly. Many such labels for incorporation into nucleic acids or coupling to nucleic acids are known. Examples of labels suitable for use in the disclosed method are radioactive isotopes, fluorescent molecules, phosphorescent molecules, enzymes, antibodies, and ligands. Preferred labels include fluors and quenchers that can be used in molecular beacon structured probes.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for simultaneous detection are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, Oreg. and Research Organics, Cleveland, Ohio.

Labeled nucleotides are a preferred form of label since they can be directly incorporated into DNA probes during synthesis. Examples of labels that can be incorporated into DNA or RNA include nucleotide analogs such as BrdUrd (Hoy and Schimke, *Mutation Research* 290:217–230 (1993)), BrdUTP (Wansick et al., *J. Cell Biology* 122:283–293 (1993)) and nucleotides modified with biotin (Langer et al., *Proc. Natl. Acad. Sci.* USA 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226–3232 (1994)). A preferred nucleotide analog detection label for DNA is BrdUTP (BUDR triphosphate, Sigma), and a preferred nucleotide analog detection label for RNA is Biotin-16-uridine-5'-triphosphate (Biotin-16-dUTP, Boehringher Mannheim). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Labels that are incorporated into nucleic acid, such as biotin, can be subsequently detected using sensitive methods well known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3,7}$]decane]-4-yl) phenyl phosphate; Tropix, Inc.).

Methods for detecting and measuring signals generated by labels are known. For example, radioactive isotopes can be detected by scintillation counting or direct visualization; fluorescent and phosphorescent molecules can be detected with a spectrophotometer or directly visualized with a camera; enzymes can be detected by visualization or detection of the product of a reaction catalyzed by the enzyme; antibodies can be detected by detecting a secondary detection label coupled to the antibody. Such methods can be used directly in the disclosed method of amplification and detection. As used herein, detection molecules are molecules which interact with amplified nucleic acid and to which one or more detection labels are coupled.

K. DNA Polymerases

DNA polymerases useful in rolling circle replication must perform rolling circle replication of primed single-stranded circles. Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of the ATC. A 5' to 3' exonuclease activity, if present, might result in the destruction of the synthesized strand. The suitability of a DNA polymerase for use in the disclosed method can be readily determined by assessing its ability to carry out rolling circle replication. Preferred rolling circle DNA polymerases are bacteriophage φ29 DNA polymerase (U.S. Pat. Nos. 5,198,543 and 5,001,050 to Blanco et al.), phage M2 DNA polymerase (Matsumoto et al., *Gene* 84:247 (1989)), phage φPRD1 DNA polymerase (Jung et al., *Proc. Natl. Acad. Sci.* USA 84:8287 (1987)), VENT® DNA polymerase (Kong et al., *J. Biol. Chem.* 268:1965–1975 (1993)), Klenow fragment of *E. coli* DNA polymerase I (Jacobsen et al., *Eur. J. Biochem.* 45:623–627 (1974)), T5 DNA polymerase (Chatterjee et al., *Gene* 97:13–19 (1991)), PRD1 DNA polymerase (Zhu and Ito, *Biochim. Biophys. Acta.* 1219:267–276 (1994)), T7 DNA polymerase (Tabor and Richardson, *J. Biol. Chem.* 262:15330–15333 (1987); Tabor and Richardson, *J. Biol. Chem.* 264:6447–6458 (1989); T7 Sequenase™ (U.S. Biochemicals)), ΔTts Polymerase (Amersham Pharmacia Biotech), and T4 DNA polymerase holoenzyme (Kaboord and Benkovic, *Curr. Biol.* 5:149–157 (1995)). φ29 DNA polymerase is most preferred. Rolling circle DNA polymerases are also generally useful for strand displacement replication.

Strand displacement can be facilitated through the use of a strand displacement factor, such as helicase. It is considered that any DNA polymerase that can perform rolling circle replication in the presence of a strand displacement factor is suitable for use in the disclosed method, even if the DNA polymerase does not perform rolling circle replication in the absence of such a factor. Strand displacement factors useful in RCA include, but are not limited to, BMRF1 polymerase accessory subunit (Tsurumi et al., *J. Virology* 67(12):7648–7653 (1993)), adenovirus DNA-binding protein (Zijderveld and van der Vliet, *J. Virology* 68(2):1158–1164 (1994)), herpes simplex viral protein ICP8 (Boehmer and Lehman, *J. Virology* 67(2):711–715 (1993); Skaliter and Lehman, *Proc. Natl. Acad. Sci.* USA 91(22):10665–10669 (1994)), single-stranded DNA binding proteins (SSB; Rigler and Romano, *J. Biol. Chem.* 270:8910–8919 (1995)), and calf thymus helicase (Siegel et al., *J. Biol. Chem.* 267:13629–13635 (1992)).

The ability of a polymerase to carry out rolling circle replication can be determined by using the polymerase in a rolling circle replication assay such as those described in Fire and Xu, *Proc. Natl. Acad. Sci.* USA 92:4641–4645 (1995).

It is possible to enhance the specificity of the DNA amplification reactions used in the disclosed method by using a DNA polymerase that is inactive at low temperature, and active only at high temperature. An example of such an enzyme, AmpliTaq Gold, has been described by Moretti et al., *Biotechniques* 25:716–722 (1998). AmpliTaq Gold is inactive until heated during the PCR before thermal cycling. A similar enzyme could be used in the disclosed method. Temperature activation of DNA polymerase also can be achieved using antibodies specific for the polymerase. For example, antibodies specific for Bst large fragment DNA polymerase could be obtained by immunization of mice. Among such antibodies, one could be chosen on the basis of its ability to bind to and inhibit the enzyme at room temperature. The antibody could also be chosen, using known screening procedures, such that upon heating, the inhibition of the DNA polymerase would cease. Combining the antibody with Bst large fragment DNA polymerase would generate an enzyme mixture that is activated upon heating.

L. Kits

Any combination of the materials useful in the disclosed method can be packaged together as a kit for performing the disclosed method. In particular, structured probes, ATCs, address probes, detection probes, and strand displacement primers are useful components of such kits. Enzymes necessary for the disclosed method are also preferred components of such kits.

METHOD

The disclosed method involves bringing into contact one or more target samples and one or more structured probes and incubating under conditions that promote hybridization between target nucleic acid sequences in the target samples and the structured probes. The structured probes may then be treated to alter, eliminate, or inactivate unhybridized probes or to stabilize the duplex region. Alternatively, hybridization between target nucleic acid sequences and the structured probes can serve to activate or make accessible the detection portion of the probe. When the detection portions of the structured probes are rolling circle replication primers, one or more ATCs and the structured probes are brought into contact, and the mixture is incubated under conditions that promote hybridization of the ATCs to the structured probes. Following this, or simultaneous with this, the ATCs and the structured probes are incubated under conditions that promote replication of the ATCs. Replication of the ATCs results in the formation of tandem sequence DNA. Alternatively, in the absence of treatment, the rolling circle replication primer can be sequestered to prevent priming of rolling circle replication.

Rolling circle replication, when used, can be combined with, or followed by additional amplification operations such as secondary DNA strand displacement, cascade strand displacement amplification, transcription, for PCR (all described in U.S. Pat. No. 5,854,033 and PCT Application No. WO 97/19193). Alternatively, hybridized structured probes also can be detected by directly detecting the detection portion (by for example, hybridizing an address probe or a detection probe to it) or using the detection portion as a primer in another type of amplification techniques such as PCR.

The structured probes form a hairpin stem and loop or curl stem and loop structure. Hybridization of the target probe portion to the target nucleic acid sequence results in disruption of the duplex region. In some forms of the disclosed method, disruption of the duplex region results in exposure of the detection portion. In other forms of the method, the unhybridized probes are treated to alter, eliminate, or inactivate them. In preferred forms of the disclosed method, the target probe portion will not hybridize to a mismatched nucleic acid sequence and therefore no conformational change will result. Only probes with duplex regions are altered or eliminated by the treatment step. Treatments include extension of the second end, cleavage of the structured probe, stabilization of the unhybridized structured probes by stabilization of the duplex region, and washing away unhybridized structured probes. Altered, stabilized, inactivated, or eliminated probes do not produce a signal or do not have functional or detectable detection portions. Thus, in the presence of matching target sequence, hybridization takes place, the duplex region is disrupted, the structured probe is not altered, stabilized, inactivated, or eliminated, and the detection portion can be detected or can mediate detection of the structured probe. In the absence of matching target sequence, hybridization does not take place, the duplex region is not disrupted, the structured probe is altered or eliminated, and the detection portion cannot be detected or cannot mediate detection of the structured probe. The hybridization of the probe to the target sequence serves as a sensitive trigger for detection of the structured probe. FIGS. 1, 2A, 2B, 2C, 2D, and 2E illustrate examples of this form of the disclosed method.

Structured probes have a larger differential in the thermal stability between a perfect match and a single nucleotide mismatch than simple linear oligonucleotides of the same sequence due to the fact that the probe with a duplex region is an intermediate form between the duplex and a fully single-stranded oligonucleotide structure. The annealing of the target probe portion of the molecule to the target can provide a physical tether for the detection signal on solid supports. It also changes the conformation of the molecule so that bound and unbound hairpins can be differentiated with the detection signal providing the eventual means of detection.

The disclosed method is useful for detection, quantitation, and/or location of any desired nucleic acid sequences. The disclosed method can be multiplexed to detect numerous different nucleic acid sequences simultaneously or in a single assay. Thus, the disclosed method is useful for detecting, assessing, quantitating, profiling, and/or cataloging RNA expression in nucleic acid samples. The disclosed method is also particularly useful for detecting and discriminating single nucleotide differences in nucleic acid sequences. This specificity is possible due to the sensitivity of duplex region stability to mismatches between target probe portions and nucleic acid sequences. Thus, the disclosed method is useful for detecting, assessing, quantitating, and/or cataloging single nucleotide polymorphisms, and other sequence differences between nucleic acids, nucleic acid samples, and sources of nucleic acid samples. In particular, the ratio of different polymorphs of a nucleic acid sequence in sample can be assessed due to the ability of the disclosed method to detect single copies of target sequences.

The disclosed method is applicable to numerous areas including, but not limited to, disease detection, mutation detection, RNA expression profiling, gene discovery, gene mapping (molecular haplotyping), agricultural research, and virus detection. Preferred uses include SNP detection in situ in cells, on microarrays, on DNA fibers, and on genomic DNA arrays; detection of RNA in cells; RNA expression profiling; molecular haplotyping; mutation detection; abnormal RNA (for example, overexpression of an oncogene or absence of expression of a tumor suppressor gene); expression in cancer cells; detection of viral genome in cells; viral RNA expression; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

A. Inactivation by Extension

Structured probes can be inactivated by adding nucleotides or a blocking molecule to the second end of the probe. This blocks the end of the probe so that it cannot have nucleotides added, makes the end of the probe non-complementary to the ATC, and/or stabilizes the duplex region. In any case, the detection portion of the probe is inactivated or otherwise prevented from being detected or mediating detection. For example, where the detection portion is a rolling circle replication primer, the structured probe cannot prime rolling circle replication of the ATC. The rolling circle replication primer sequence is at an end of the structured probe. This primer sequence can hybridize to the primer complement portion of an ATC and prime rolling circle replication of the ATC. Such priming requires that the terminal nucleotides be hybridized to the ATC. Extension inactivation prevents this terminal hybridization.

For extension inactivation, it is preferred that the second complementary portion of the probe be at the second end of the probe and that the first complementary portion be away from the first end of the probe such that there is a region at the first end of the probe not in the duplex region. This arrangement provides a template, the region at the first end of the probe beyond the first complementary portion, beyond the 3' end of the second complementary portion. The probe can then be altered, and thus inactivated, by extending the second end of the probe using the portion of the probe extending beyond the first complementary portion as a template. Only probes with intact duplex regions are extended. This is because the second end of the probe will not be hybridized next to the first end of the probe if the duplex region has been disrupted. Examples of extension are shown in FIGS. 1, 2D, and 2E. In some forms of the method, the result of extension is that the second end sequence of the extended probe is not complementary to the primer complement portion of the ATC and cannot prime replication of the ATC. This is illustrated in FIGS. 1 and 2E.

The structured probe also can be inactivated by capping the second end of the probe through the addition of a chain-terminating nucleotide. This is illustrated in FIG. 2D. The structured probes or the target nucleic acid sequences can be associated with a solid support when using extension inactivation.

B. Inactivation by Cleavage

Structured probes can be inactivated by cleaving the probe. Preferably, the structured probe contains a nucleic acid cleavage site. Cleavage separates the detection portion so that it will not be present for detection. For this form of the method it is preferred that the detection portion not overlap the nucleic acid cleavage site with the result being that the nucleic acid cleavage site is closer to the first end of the probe than the detection portion. The probe can be altered, and thus inactivated, by cleavage of the nucleic acid cleavage site in the probe. It is preferred that the cleavage site be in the duplex region. It is also preferred that only probes with intact duplex regions are cleaved. This is easy to accomplish since many double strand-dependent nucleases are known (such as restriction endonucleases). Cleavage inactivation of a structured probe is illustrated in FIG. 2C.

Where the detection portion is a rolling circle replication primer, it is preferred that the structured probe be designed so that the rolling circle replication primer portion does not overlap the second complementary portion. This prevents residual rolling circle replication primer sequences from remaining at the second end of the probe after cleavage (where they could function to prime rolling circle replication). However, a short, partial overlap is possible where the cleavage site remains upstream of (that is, closer to the first end than) the rolling circle replication primer portion or where the portion of the rolling circle replication primer sequences remaining after cleavage are too short to form a hybrid with the ATC that can support replication. When the rolling circle replication primer portion does not overlap the second complementary portion, the second complementary portion is placed closer to the first end of the probe than the rolling circle replication primer portion.

It is preferred that the nucleic acid cleavage site be a restriction site, and that the site be cleaved with a restriction enzyme. The structured probes or the target nucleic acid sequences can be associated with a solid support when using cleavage inactivation.

C. Inactivation by Ligand Binding

Structured probes can be inactivated by binding of ligand to the probe. It is preferred that the structured probe contain a protein/nucleic acid binding site, such as a restriction endonuclease recognition site. Binding of inactive restriction endonuclease to the duplex region of an unhybridized probe molecule stabilizes the duplex region so that the detection portion will not be available for detection. For this form of the method it is preferred that the binding recognition sequence be in the duplex region and that the detection portion partially overlap with the binding site so that the part of the detection sequence remaining unhybridized after ligand binding is too short to support detection. It is preferred that the binding site be close to or at the 3' end. Only probes with duplex regions are stabilized by the binding of inactive restriction endonuclease. This is easy to accomplish since several double strand-dependent nucleases, such as restriction endonucleases, are available as inactive mutants. In addition, many nucleases can be rendered capable of binding but not cutting by using specific experimental conditions.

Where the detection portion is a rolling circle replication primer, it is preferred that the structured probe be designed so that the detection portion overlaps the first complementary portion. This permits the rolling circle replication primer sequences to be trapped within the stabilized duplex region. It is preferred that the binding site be a restriction endonuclease cleavage site, and that the site be bound but not cleaved by a restriction enzyme. The structured probes or the target nucleic acid sequences can be associated with a solid support when using inactivation by binding.

D. Elimination by Washing

Unhybridized structured probes also can be prevented from priming rolling circle replication by simply separating them, preferably by washing, from structured probes hybridized to target sequences. For this form of the method, it is preferred that the target nucleic acid sequences be associated with a solid support. Hybridization between target nucleic acid sequences in the target samples and the structured probes then associates the probe with the solid support, and the unhybridized probes can be washed away. This is illustrated in FIG. 2A.

In this form of the method, the structured probe can be designed so that the detection portion either overlaps or does not overlap the second complementary portion. The overlap can be partial—where only a portion of the detection portion overlaps the second complementary portion—or complete—where the detection portion and the second complementary portion are the same portion of the probe. When the detection portion does not overlap the second complementary portion, the second complementary portion is preferably placed closer to the first end of the probe than the detection portion. Where the detection portion partially overlaps the second complementary portion, a part of the detection portion can extend beyond the second complementary portion toward the first end into the loop. The target nucleic acid sequences can be associated with a solid support when structured probes are eliminated by washing.

E. Sequestration

Structured probes also can be prevented from being detected by sequestering the detection portion in a duplex region unless the duplex region is disrupted by hybridization of the probe to the target nucleic acid sequence. Careful design of the structured probe and the use of appropriate conditions during detection will leave the duplex region of unhybridized probes intact.

Sequestration can be accomplished by having a complete or significant overlap between the detection portion and the second complementary portion. Preferably, the detection portion and the second complementary portion are the same portion of the probe. Where there is a partial overlap, a portion of the detection portion extends beyond the second complementary portion toward the first end and into the loop. In this case, the non-overlapping portion should be short enough such that the detection portion cannot be detected nor mediate detection. Where the detection portion is a rolling circle replication primer, the non-overlapping portion should be short enough such that hybridization of the ATC to the portion of the rolling circle replication primer portion that is in the loop will not disrupt the duplex region. The rolling circle replication primer, if used, should not extend closer to the second end than the second complementary portion. Alternatively, if the rolling circle replication primer should extend closer to the second end than the second complementary portion, the portion of the rolling circle replication primer sequences in the loop should be too short to form a hybrid with the ATC that can support replication. The structured probes or the target nucleic acid sequences can be associated with a solid support when using sequestration.

F. Detection

Structured probes can be detected via their detection portions, either directly or indirectly. The detection portion can itself generate a signal, can mediate generation of a signal or amplification, and/or mediate association of a signal with the structured probe. A preferred form of detection involves rolling circle replication primed by a rolling circle replication primer (where the rolling circle replication primer is the detection portion).

For multiplex forms of the method (that is, forms where multiple target sequences are detected in the same assay), a plurality of different structured probes are mixed with at least one target sample. Preferably, the target probe portions of each different structured probe are complementary to different target sequences and the detection portions of each different structured probe are complementary to different ATCs, detector probes, or address probes. Alternatively, the detection portions of at least two different probes can be complementary to the same ATC, detector probe, or address probe.

Different target nucleic acid sequences need not be detected using a unique detection portion sequence for each structured probe designed for a different target sequence. That is, the sequence of the detection portion can be the same for groups of structured probes targeted to different sequences. Such matching sequences will be detected together as a group. For example, where the detection portion is a rolling circle replication primer, matching primer sequences can prime replication of the same ATC. This will result in a single form of tandem sequence DNA produced when any of the group of target sequences are present. Matching detection portions are useful, for example, to detect any one (or more) of a set of mutations in a gene. For example, some oncogenes can have numerous different mutations that are cancer-associated, and it would be useful to streamline detection of any one of them. Where multiple target sequences are associated with the same detection portion sequences, the target probe portion sequences will, of course, be unique for each target sequence.

In this form of the method, a plurality of different target samples each can be mixed with at least one type of structured probe. Preferably, the detection portions of the probes mixed with different target samples are complementary to different ATCs, detection probes, or address probes. Two or more of the target samples can be mixed together after the probes have been added. In one embodiment of this form of the method, the set of structured probes mixed with each different target sample can be complementary to the same set of target sequences.

The same target sequence also can be targeted by multiple structured probes. That is, different probes having different detection portion sequences can be targeted to the same nucleic acid sequence. This is useful, for example, for detection of the same sequence in multiple samples in a single assay. For this, each different sample can be mixed with a different structured probe. This will associate a different detection portion sequence with the target sequence based on the source of the target sequence (that is, based on which sample the target sequence came from). The result will be a unique signal for the target sequence from each source. In this way, the source of each target sequence can be determined even after the target samples are mixed together. Such mixing simplifies the manipulations needed for this type of assay.

The method is particularly useful for detecting single nucleotide differences between sequences. Some sequences are polymorphic. As used herein, a polymorphic sequence is a sequence that has different forms (that is, differs in sequence) in different sources of the sequence. For example, one individual may have a gene having an A at a certain position and another individual may have a C at the same position in the same gene. These genes thus have a polymorphic sequence. The A and the C in these genes are polymorphic nucleotides. A polymorphic nucleotide is a nucleotide that differs between at least two forms of a polymorphic sequence. Put another way, the nucleotide position of the A and C is a polymorphic nucleotide position.

The disclosed method can be used to distinguish between these two forms of the genes based on this single difference. This can be accomplished, for example, by designing structured probes with target probe portions complementary to each of the gene forms. Only exact complementarity between the target probe portion and the target nucleic acid sequence will result in hybridization that disrupts the duplex region in the structured probe. Thus, signal detection will only occur from a given probe if its cognate target sequence is present.

G. Rolling Circle Amplification

Structured probes using a rolling circle replication primer the detector portion can prime rolling circle replication when the structured probes are hybridized to their cognate target nucleic acid sequences. For rolling circle replication, DNA polymerase is mixed with the probes and ATCs (hybridized to the rolling circle replication primer portion) and incubated under conditions that promote replication of the ATCs. Replication of the ATC results in the formation of a long DNA strand containing numerous tandem repeats of the ATC sequence (the DNA is referred to as tandem sequence DNA). Unique identification of multiple nucleic acid sequences in a single assay is accomplished by associating unique rolling circle replication primer sequences with each of the various nucleic acid sequences to be detected. Each rolling circle replication primer sequence hybridizes to, and primes replication of, a unique ATC. Detection of the unique sequences of the various resulting tandem sequence DNAs (each derived from a different, nucleic acid sequence-specific ATC) indicates the presence in the nucleic acid sample of the target sequence corresponding to that TS-DNA sequence.

H. Molecular Beacon Structured Probes

Molecular beacons make use of fluorescent moieties where the fluorescent moieties fluoresce most strongly when the fluorescent moiety and a quencher moiety are not in proximity (Tyagi and Kramer, *Nature Biotechnol.* 14:303–309 (1995)). This principle can be used for detecting structured probes hybridized to their cognate target sequences by, for example, associating a fluor and a quencher with a structured probe. Specifically, the fluor should be associated with one of the complementary portions of a structured probe and the quencher with another complementary portion of the structured probe such that when a duplex region is formed by the structured probe the fluor is quenched. Alternatively, the structured probe need not have a separate quencher where hybridization of the complementary portion associated with the fluor causes the fluor to be quenched. Quenching refers to a reduction in the fluorescence of the fluor. Quenching need not eliminate or totally extinct the fluorescence. Preferred molecular beacon structured probes are curl structured probes.

FIG. 1 is a diagram of an example of the disclosed method involving 3' extension to inactivate the structured probe. The detection portion overlaps part of the second complementary portion and a 5' single-stranded tail extends beyond the first complementary portion (involved in a duplex region with the second complementary portion). Hybridization of the target probe portion (in the loop region of the probe) to a target sequence disrupts the duplex region (hairpin-1; second panel). A structured probe mismatched to a prospective target sequence does not hybridize and its duplex region is not disrupted (hairpin-2; second panel). A fill-in reaction fills in the 5' single-stranded tail of structured probes with intact duplex regions (hairpin-2; third panel). The fill-in reaction does not affect the structured probe with a disrupted duplex region (hairpin-1; third panel). ATCs hybridize to the detection portion (a rolling circle replication primer exposed upon disruption of the duplex region) of structured probes with disrupted duplex regions (hairpin-1; fourth panel). Structured probes not hybridized to the target sequence have intact duplex regions and cannot hybridize to the ATCs (hairpin-2; fourth panel). Hybridized ATCs are amplified by rolling circle replication primed from the rolling circle replication primer (hairpin-1; fifth panel). Structured probes with intact, filled-in duplex regions do not amplify the ATC (hairpin-2; fifth panel). The filled-in structured probe could not amplify the ATC even if it did hybridize since the filled-in 3' end of the structured probe is not complementary to the ATC.

Figure 2:
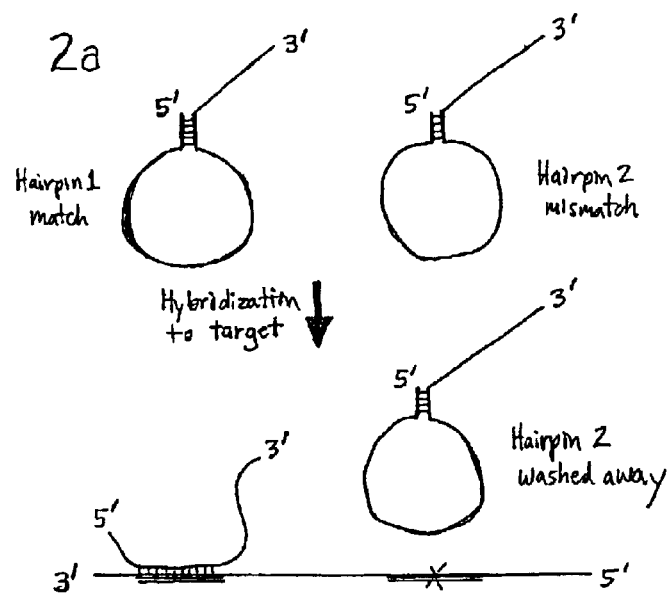
FIGS. 2A–2E are diagrams of examples of the disclosed structured probes and method. The diagrams show the hybridization and treatment steps but not signal amplification or detection.
Figure 2:
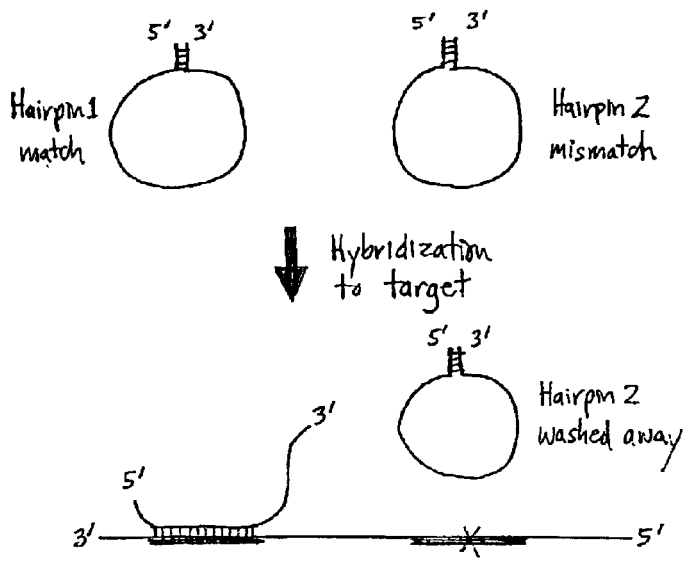
Figure 2:
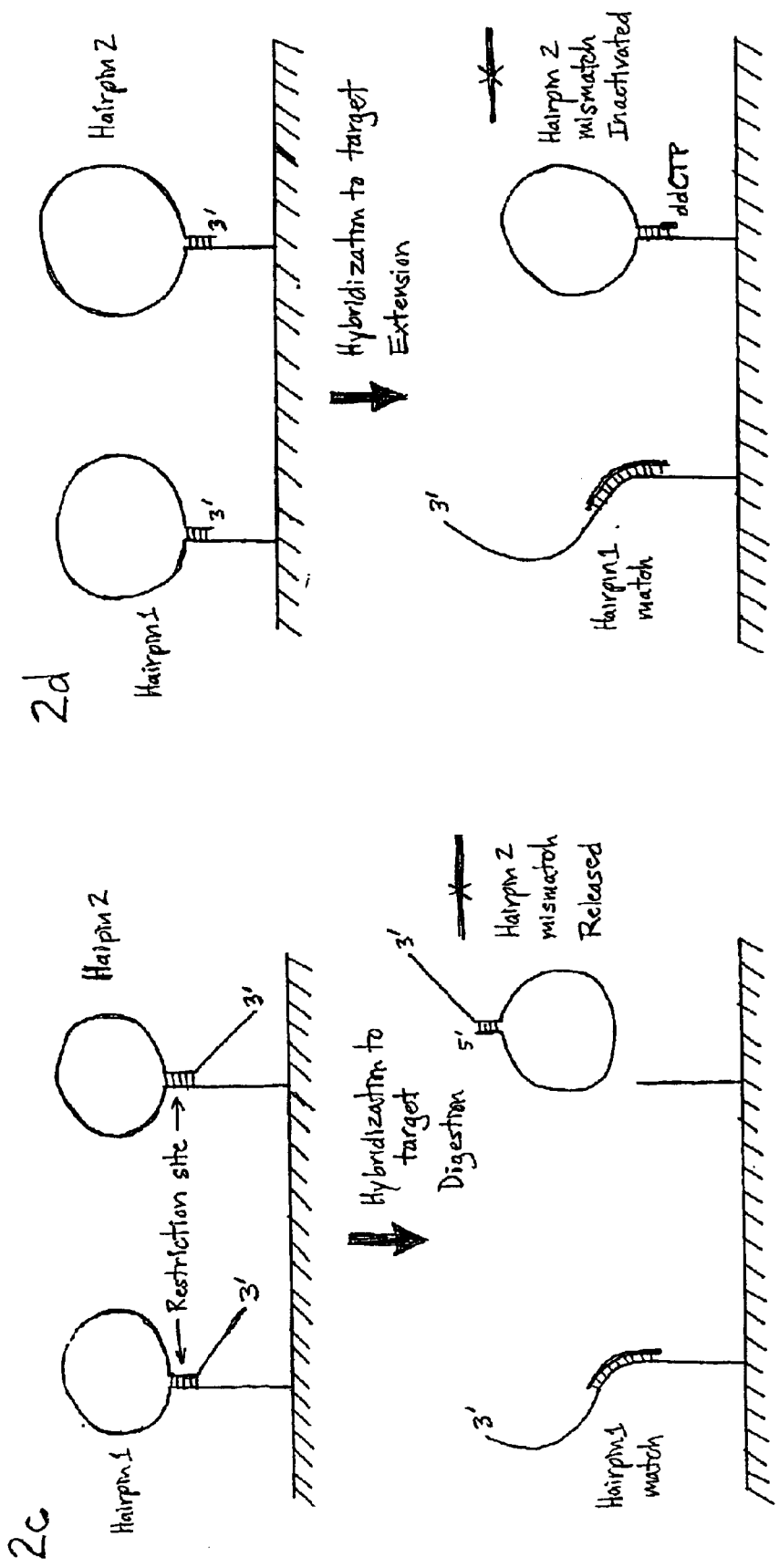
Figure 2:
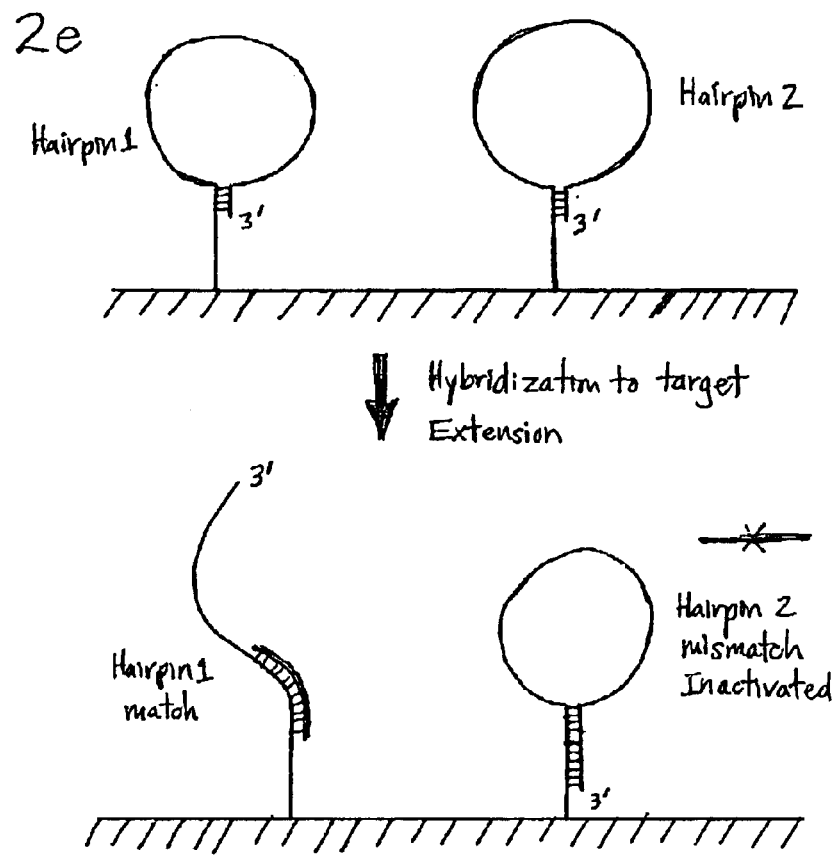

FIGS. 2A–2E are diagrams of examples of the disclosed structured probes and method. Five alternative forms of the detector oligonucleotide are shown in FIGS. 2A–2E. In the structured probe shown in FIG. 2A, the loop contained within the hairpin structure contains only the sequence complementary to the target sequence and the primer sequence is attached outside the hairpin domain. When this version is used, it is necessary to remove excess primer molecules by washing before amplification. In FIG. 2B, the loop structure contains approximately half of the detection portion while the other half of the detection portion is included in one side of the pairing bases with only a few bases outside the duplex region. It is possible to hybridize the detector and proceed with detection without removing the excess probe since the number of bases within the loop that are complementary to the ATC (or detection probe or address probe) should be insufficient to cause the structural transition to the linear form required for the primer to function. In FIG. 2C, the detection portion is outside the loop and a restriction endonuclease site is present in the duplex region. This necessitates the use of this probe design in array or in situ formats where the clipped-off primer sequence can be removed by washing. In FIG. 2D, the structured probe has an extension at its 5' end (that is, the first end). When the duplex region is formed, the 3' end (that is, the second end) of the probe can be extended using the 5' part of the probe as template. If an ATC is used which has biased nucleotide content (for example, a G-less circle), the 3' end of the probe can be filled using the nucleotide that is not needed for rolling circle amplification using the 5' part of the probe as template (providing the structured probe is not hybridized to the target sequence, in which case the duplex region would be disrupted). By using a dideoxy form of the nucleotide, the 3' end can be rendered incapable of further extension. Alternatively, if the 5' end is not complementary to the ATC, all four nucleotides can be used to extend the 3' end of the unhybridized probe (FIG. 2E). This will also create a structured probe structure that cannot be extended using the ATC, because the melting temperature of the duplex region will be increased and the 3' end of the primer sequence will no longer match the ATC. An additional design is analogous to the structures shown in FIG. 2 except that the loop has reverse polarity (3'-3' oligonucleotide structure). This is the curl structured probe design (FIG. 3B). This permits simultaneous extension of the oligonucleotide sequences matching the target sequence and the sequences matching the ATC. This will provide increased stability of binding to the target.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A method of detecting target nucleic acid sequences, the method comprising
   (a) bringing into contact one or more target samples and one or more structured probes, and incubating under conditions that promote hybridization between target nucleic acid sequences in the target samples and the structured probes, wherein each structured probe is bifunctional, wherein one function is as a probe to a target nucleic acid sequence and the other function is a detection function, wherein the detection function is not possible unless the probe hybridizes to the target nucleic acid sequence,
   wherein each structured probe has a first end and a second end, wherein each structured probe comprises at least two complementary portions, a target probe portion, and a detection portion, wherein the two or more complementary portions comprise a first complementary portion and a second complementary portion, wherein two or more of the complementary portions form a duplex region, wherein formation of the duplex region forms a loop, wherein at least a portion of the target probe portion is in the loop, wherein hybridization of the target probe portion to the target nucleic acid sequence disrupts the duplex region, (b) detecting the structured probes, wherein, prior to detection, the structured probes are treated to alter unhybridized probes, wherein only probes with intact duplex regions are altered by treatment of the structured probes, wherein altered probes are not detected.

2. The method of claim 1 wherein the second complementary portion of at least one probe is at the second end of the probe, wherein the first complementary portion is not at the first end of the probe, wherein the treatment is extending the second end of the probe using the portion of the probe closer to the first end of the probe than the first complementary portion as template, wherein only probes with intact duplex regions are extended.

3. The method of claim 2 wherein the second end sequence of the extended probe is not complementary to the primer complement portion of an amplification target circle and cannot prime replication of the amplification target circle.

4. The method of claim 2 wherein during extension the second end of the probe is capped by addition of a chain-terminating nucleotide such that the probe cannot prime nucleic acid synthesis.

5. The method of claim 2 wherein the target nucleic acid sequences are associated with a solid support, wherein hybridization between target nucleic acid sequences in the target samples and the structured probes associates the probe with the solid support.

6. The method of claim 2 wherein the probes are associated with a solid support.

7. The method of claim 6 wherein the first ends of the probes are coupled to the solid support.

8. The method of claim 2 wherein a portion of the detection portion extends beyond the second complementary portion toward the first end and is in the loop.

9. The method of claim 2 wherein the detection portion and the second complementary portion are the same portion of the probe.

10. The method of claim 2 wherein extension of the second end of the probe makes the detection portion non-functional, reduces or eliminates the detectability of the detection portion, or a combination.

11. The method of claim 1 wherein the duplex region of at least one probe comprises a nucleic acid cleavage site, wherein the treatment is cleavage of the nucleic acid cleavage site, wherein only probes with intact duplex regions are cleaved.

12. The method of claim 11 wherein the detection portion does not overlap the nucleic acid cleavage site such that the nucleic acid cleavage site is closer to the first end of the probe than the detection portion.

13. The method of claim 11 wherein the detection portion does not overlap the second complementary portion such that the second complementary portion is closer to the first end of the probe than the detection portion, wherein the duplex region comprises a nucleic acid cleavage site.

14. The method of claim 11 wherein the nucleic acid cleavage site is a restriction site, wherein the site is cleaved with a restriction enzyme.

15. The method of claim 11 wherein the probes are associated with a solid support.

16. The method of claim 15 wherein the first ends of the probes are coupled to the solid support.

17. The method of claim 11 wherein the detection portion partially overlaps the second complementary portion.

18. The method of claim 17 wherein the second complementary portion is not at the second end of the probe.

19. The method of claim 11 wherein cleavage of the nucleic acid cleavage site eliminates the detection portion from the probe, makes the detection portion non-functional, reduces or eliminates the detectability of the detection portion, or a combination.

20. The method of claim 1 wherein structured probes with intact duplex regions are not detected.

21. The method of claim 20 wherein the detection portion and the second complementary portion are the same portion of the probe.

22. The method of claim 20 wherein a portion of the detection portion extends beyond the second complementary portion toward the first end and is in the loop, wherein hybridization of an amplification target circle to the portion of the detection portion that is in the loop will not disrupt the duplex region.

23. The method of claim 20 wherein the target nucleic acid sequences are associated with a solid support, wherein hybridization between target nucleic acid sequences in the target samples and the structured probes associates the probe with the solid support.

24. The method of claim 1 wherein the duplex region and loop is a hairpin stem and loop structure.

25. The method of claim 24 wherein the first end of the structured probe is a 5' end and the second end of the structured probe is a 3' end.

26. The method of claim 25 wherein the second complementary portion, the first complementary portion, the target probe portion, and the detection portion are each in a 5' to 3' orientation relative to the first end.

27. The method of claim 1 wherein the duplex region and loop is a curl stem and loop structure.

28. The method of claim 27 wherein the first end of the structured probe is a 3' end and the second end of the structured probe is a 3' end.

29. The method of claim 28 wherein there is a 5' to 5' junction between (a) the second complementary portion and detection portion and (b) the target probe portion.

30. The method of claim 29 wherein the second complementary portion and detection portion are each in a 3' to 5' orientation relative to the second end, and wherein the target probe portion and first complementary portion are each in a 3' to 5' orientation relative to the first end.

31. The method of claim 28 wherein there is a 5' to 5' junction between the target probe portion and the first complementary portion.

32. The method of claim 31 wherein the second complementary portion, detection portion, and target probe portion are each in a 3' to 5' orientation relative to the second end, and wherein the first complementary portion is in a 3' to 5' orientation relative to the first end.

33. The method of claim 1 wherein the detection portion comprises a rolling circle replication primer.

34. The method of claim 33 wherein detection of the structured probes is accomplished by, bringing into contact one or more amplification target circles and the structured probes, and incubating under conditions that promote hybridization of the amplification target circles to the structured probes, incubating the amplification target circles and the structured probes under conditions that promote replication of the amplification target circles, wherein replication of the amplification target circles results in the formation of tandem sequence DNA.

35. The method of claim 34 wherein, prior to detection, the structured probes are treated to alter unhybridized probes,
wherein only probes with intact duplex regions are altered by treatment of the structured probes, wherein altered probes do not prime replication of the amplification target circles.

36. The method of claim 35 wherein structured probes with intact duplex regions do not prime replication of the amplification target circles.

37. The method of claim 1 wherein at least one of the target nucleic acid sequences or at least one of the structured probes is associated with a solid support.

38. The method of claim 37 wherein the first ends of the probes are coupled to the solid support.

39. The method of claim 37 wherein each of the target nucleic acid sequences or structured probes is located in a different predefined region of the solid support.

40. The method of claim 39 wherein the distance between the different predefined regions of the solid support is fixed.

41. The method of claim 40 wherein the solid support comprises thin film, membrane, bottles, dishes, fibers, woven fibers, shaped polymers, particles, beads, microparticles, or a combination.

42. The method of claim 39 wherein the distance between at least two of the different predefined regions of the solid support is variable.

43. The method of claim 42 wherein the solid support comprises at least one thin film, membrane, bottle, dish, fiber, woven fiber, shaped polymer, particle, bead, or microparticle.

44. The method of claim 43 wherein the solid support comprises at least two thin films, membranes, bottles, dishes, fibers, woven fibers, shaped polymers, particles, beads, microparticles, or a combination.

45. The method of claim 39 wherein each of the target nucleic acid sequences is located in a different predefined region of the solid support, wherein the location on the solid support where the structured probes are detected indicates the presence in the target sample of the target nucleic acid sequence corresponding to that region of the solid support.

46. The method of claim 39 wherein each of the structured probes is located in a different predefined region of the solid support, wherein the location on the solid support where the structured probes are detected indicates the presence in the target sample of the target nucleic acid sequence corresponding to the structured probe at that region of the solid support.

47. The method of claim 37 wherein the solid support comprises a plurality of target nucleic acid sequences located in a plurality of different predefined regions of the solid support, wherein the target nucleic acid sequences collectively correspond to a plurality of structured probes.

48. The method of claim 37 wherein the solid support comprises a plurality of structured probes located in a plurality of different predefined regions of the solid support, wherein the structured probes collectively correspond to a plurality of target nucleic acid sequences.

49. The method of claim 37 wherein the solid support comprises thin film, membrane, bottles, dishes, fibers, woven fibers, shaped polymers, particles, beads, microparticles, or a combination.

50. The method of claim 37 wherein the solid support comprises acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, or polyamino acids.

51. The method of claim 37 wherein the solid support is porous.

52. The method of claim 1 wherein the target probe portion will not hybridize to a mismatched nucleic acid sequence, wherein the mismatched nucleic acid sequence will not disrupt the duplex region.

53. The method of claim 1 wherein the treatment is extending the second end of the probe using probe sequence as template.

54. The method of claim 53 wherein the duplex region is a curl stem and loop structure.

55. A method of detecting target nucleic acid sequences, the method comprising
(a) bringing into contact one or more target samples and one or more structured probes, and incubating under conditions that promote hybridization between target nucleic acid sequences in the target samples and the structured probes, wherein each structured probe is bifunctional, wherein one function is as a probe to a target nucleic acid sequence and the other function is a detection function, wherein the detection function is not possible unless the probe hybridizes to the target nucleic acid sequence,
wherein each structured probe has a first end and a second end, wherein each structured probe comprises at least two complementary portions, a target probe portion, and a detection portion, wherein the two or more complementary portions comprise a first complementary portion and a second complementary portion,
wherein two or more of the complementary portions form a duplex region, wherein formation of the duplex region forms a loop, wherein at least a portion of the target probe portion is in the loop, wherein hybridization of the target probe portion to the target nucleic acid sequence disrupts the duplex region,
(b) detecting the structured probes,
wherein, prior to detection, the structured probes are treated to alter unhybridized probes, wherein the treatment is extending the second end of the probe using probe sequence as template,
wherein only probes with intact duplex regions are altered by treatment of the structured probes, wherein altered probes are not detected.

56. A method of detecting target nucleic acid sequences, the method comprising
(a) bringing into contact one or more target samples and one or more structured probes, and incubating under conditions that promote hybridization between target nucleic acid sequences in the target samples and the structured probes, wherein each structured probe is bifunctional, wherein one function is as a probe to a target nucleic acid sequence and the other function is a detection function, wherein the detection function is not possible unless the probe hybridizes to the target nucleic acid sequence,
wherein each structured probe has a first end and a second end, wherein each structured probe comprises at least two complementary portions, a target probe portion, and a detection portion, wherein the two or more complementary portions comprise a first complementary portion and a second complementary portion, wherein two or more of the complementary portions interact with each other to form a duplex region, wherein formation of the duplex region forms a loop, wherein at least a portion of the target probe portion is in the loop, wherein hybridization of the target probe portion to the target nucleic acid sequence disrupts the duplex region, (b) detecting the structured probes, wherein, prior to detection, the structured probes are treated to alter unhybridized probes, wherein only probes with the duplex region intact are altered by the treatment of the structured probes, whereby altered probes are not detected.

* * * * *